(12) United States Patent
Estes

(10) Patent No.: US 9,731,072 B2
(45) Date of Patent: *Aug. 15, 2017

(54) INFUSION PUMP SYSTEM

(71) Applicant: Bigfoot Biomedical, Inc., Milpitas, CA (US)

(72) Inventor: Mark C. Estes, Malibu, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 329 days.

This patent is subject to a terminal disclaimer.

(21) Appl. No.: 14/339,642

(22) Filed: Jul. 24, 2014

(65) Prior Publication Data

US 2014/0336570 A1    Nov. 13, 2014

Related U.S. Application Data

(60) Continuation of application No. 13/613,620, filed on Sep. 13, 2012, now Pat. No. 8,790,294, which is a
(Continued)

(51) Int. Cl.
*A61M 5/172*    (2006.01)
*A61M 5/142*    (2006.01)
*A61M 5/168*    (2006.01)

(52) U.S. Cl.
CPC ...... *A61M 5/1723* (2013.01); *A61M 5/14244* (2013.01); *A61M 5/16831* (2013.01);
(Continued)

(58) Field of Classification Search
CPC ............ A61M 5/1723; A61M 5/16831; A61M 5/14244; A61M 2205/502; A61M 2205/18; A61M 2202/07; A61M 2205/3306
See application file for complete search history.

(56) References Cited

U.S. PATENT DOCUMENTS 5,984,894 A    11/1999 Poulsen
6,551,276 B1    4/2003 Mann et al.
(Continued)

FOREIGN PATENT DOCUMENTS

EP    0-062-974    10/1982
EP    0-275-213    7/1988
(Continued)

OTHER PUBLICATIONS

"Which Insulin Pump is Right for Me?", Albany Medical Center, Goodman Diabetes Service, Jan. 2006, 4 pages.
(Continued)

*Primary Examiner* — Kevin C Sirmons
*Assistant Examiner* — Amber Stiles
(74) *Attorney, Agent, or Firm* — Fish & Richardson P.C.

(57) ABSTRACT

Some embodiments of a portable infusion pump system can be configured to can be configured to adjust the sensitivity of particular detectors or alert systems based (at least in part) on information received from a monitoring device. For example, a glucose monitoring device can communication with an infusion pump assembly used to supply insulin or another medication to a user. In such circumstances, the data received from the monitoring device can be used to adjust the sensitivity of an occlusion detection system.

20 Claims, 14 Drawing Sheets

Related U.S. Application Data continuation of application No. 13/072,874, filed on Mar. 28, 2011, now Pat. No. 8,277,435, which is a division of application No. 12/115,008, filed on May 5, 2008, now Pat. No. 7,938,797.

(52) U.S. Cl.
CPC ..... *A61M 2202/07* (2013.01); *A61M 2205/18* (2013.01); *A61M 2205/3306* (2013.01); *A61M 2205/502* (2013.01)

(56) References Cited

U.S. PATENT DOCUMENTS

| | | | |
|---|---|---|---|
| 6,554,798 B1 | 4/2003 | Mann et al. | |
| 6,659,978 B1 | 12/2003 | Kasuga | |
| 6,691,043 B2 | 2/2004 | Ribeiro, Jr. | |
| 6,744,350 B2 | 6/2004 | Blomquist | |
| 6,852,104 B2 | 2/2005 | Blomquist | |
| 6,925,393 B1 | 8/2005 | Kalatz et al. | |
| 6,936,029 B2 | 8/2005 | Mann et al. | |
| 6,979,326 B2 | 12/2005 | Mann et al. | |
| 6,997,920 B2 | 2/2006 | Mann et al. | |
| 7,025,743 B2 | 4/2006 | Mann et al. | |
| 7,109,878 B2 | 9/2006 | Mann et al. | |
| 7,278,983 B2 | 10/2007 | Ireland et al. | |
| 7,938,797 B2 * | 5/2011 | Estes | A61M 5/14244 604/503 |
| 8,277,435 B2 * | 10/2012 | Estes | A61M 5/14244 604/503 |
| 8,790,294 B2 * | 7/2014 | Estes | A61M 5/14244 604/66 |
| 2004/0167464 A1 * | 8/2004 | Ireland | A61M 5/14244 604/66 |
| 2004/0176720 A1 | 9/2004 | Kipfer | |
| 2007/0062250 A1 * | 3/2007 | Krulevitch | A61M 5/16831 73/1.16 |
| 2007/0073228 A1 | 3/2007 | Mernoe et al. | |
| 2007/0073235 A1 * | 3/2007 | Estes | A61M 5/14244 604/151 |
| 2007/0073236 A1 | 3/2007 | Mernoe et al. | |
| 2007/0118405 A1 | 5/2007 | Campbell et al. | |
| 2007/0167912 A1 | 7/2007 | Causey et al. | |
| 2007/0173761 A1 | 7/2007 | Kanderian, Jr. et al. | |
| 2007/0179444 A1 | 8/2007 | Causey et al. | |
| 2008/0125700 A1 | 5/2008 | Moberg et al. | |
| 2008/0294142 A1 | 11/2008 | Patel et al. | |

FOREIGN PATENT DOCUMENTS

| | | |
|---|---|---|
| EP | 1-045-146 | 12/2000 |
| EP | 1 818 664 | 8/2007 |
| WO | WO 2004/056412 | 7/2004 |
| WO | WO 2004/110526 A | 12/2004 |

OTHER PUBLICATIONS

"Using the Deltec Cozmo Insulin Pump Correction Bolus Feature" believed to be publicly available before May 5, 2008, pp. 36-41.
International Search Report and Written Opinion, PCT/US2009/042817, mailed Sep. 3, 2009, 14 pages.

* cited by examiner

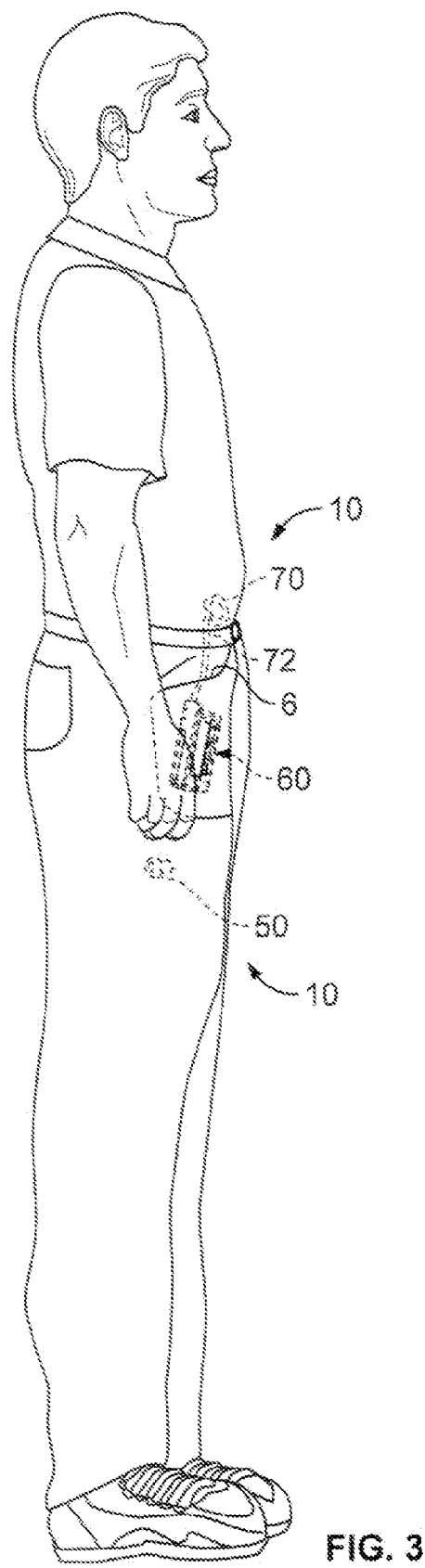
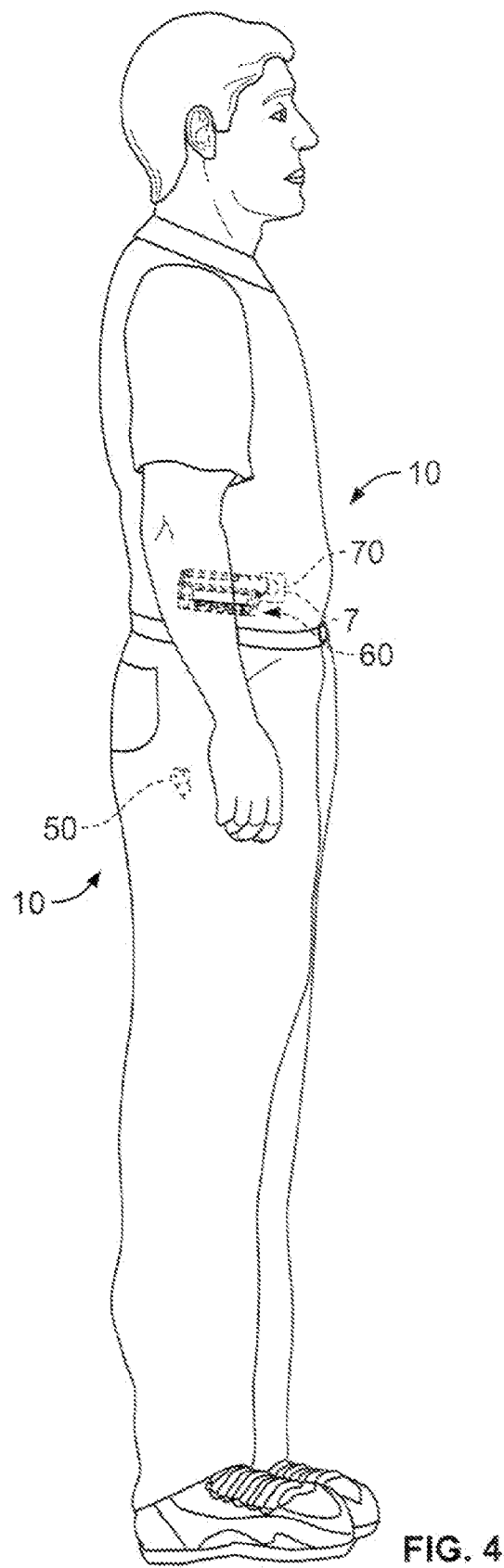
FIG. 3
FIG. 4

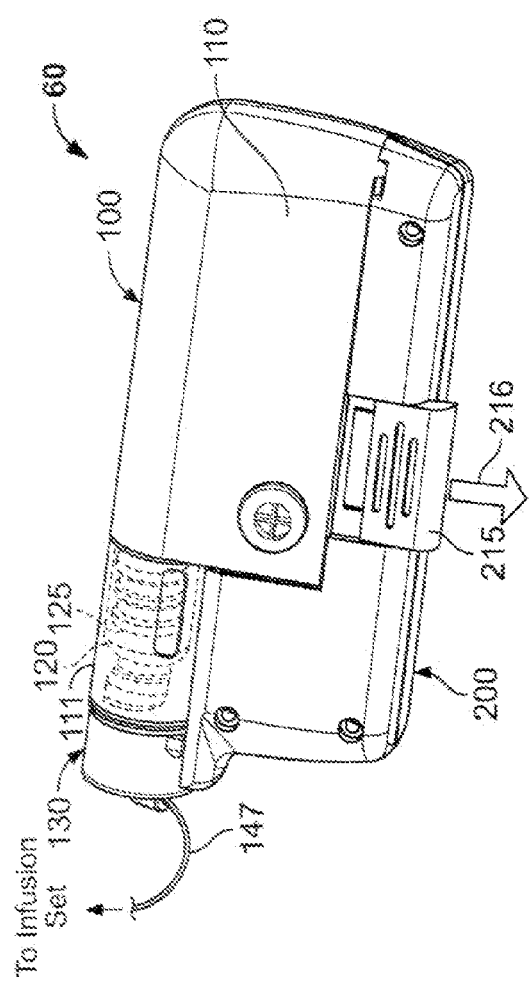
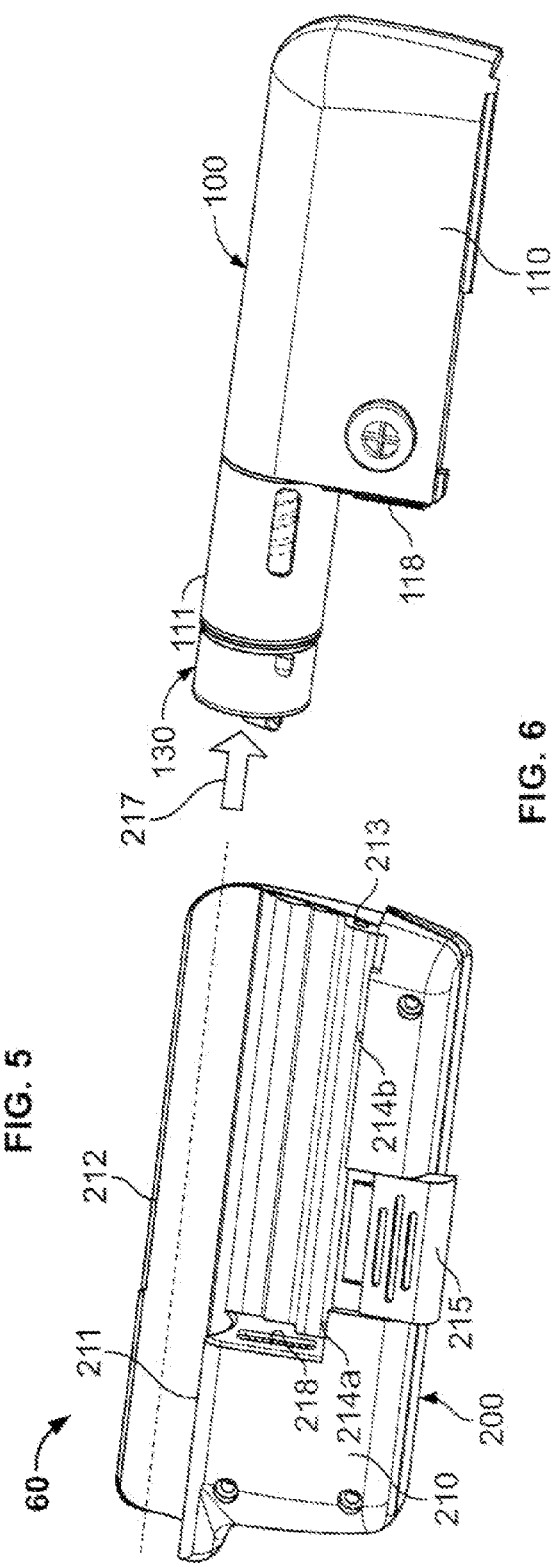

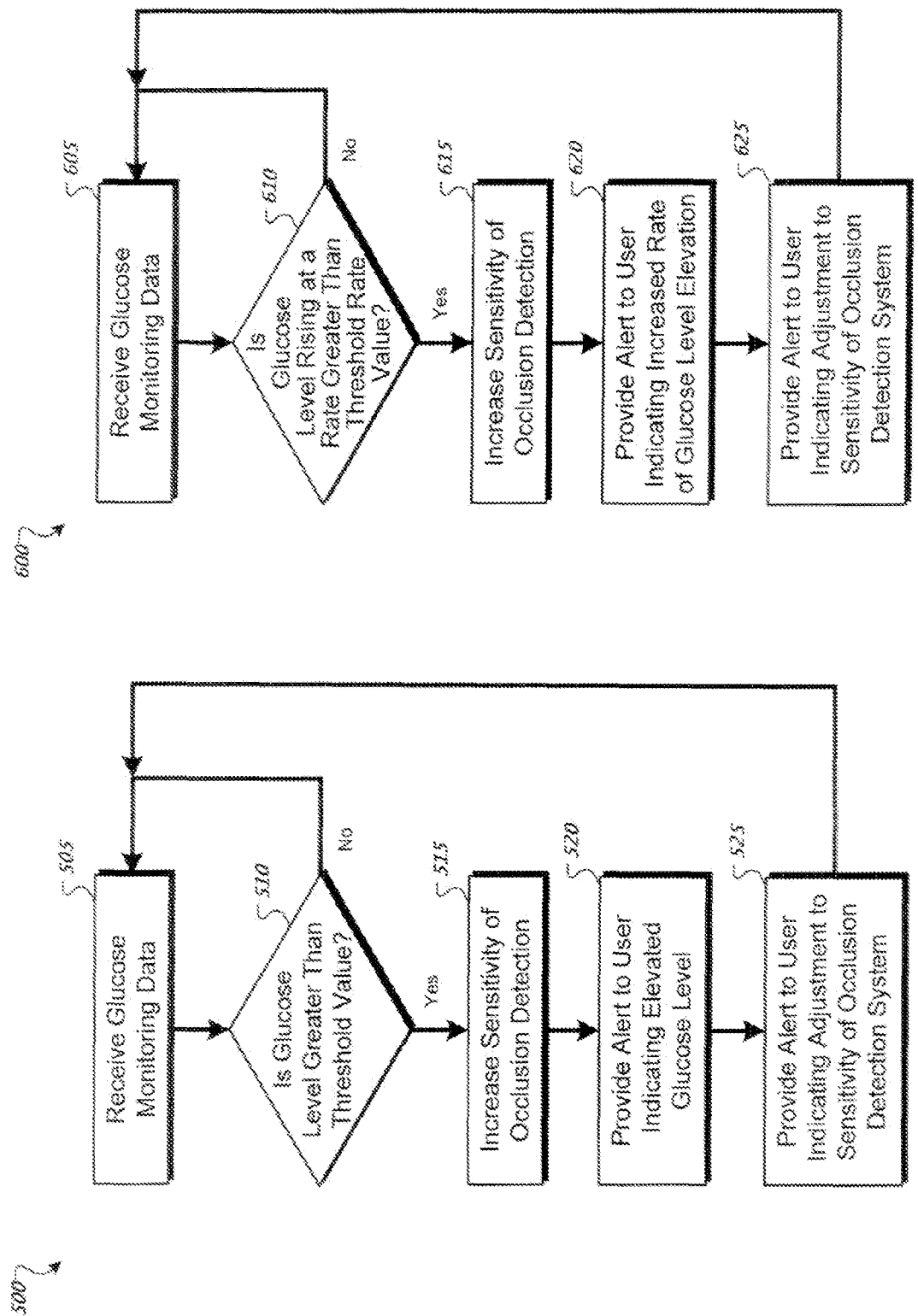

INFUSION PUMP SYSTEM

CROSS-REFERENCE TO RELATED APPLICATION(S)

This is a continuation of U.S. application Ser. No. 13/613,620 filed Sep. 13, 2012 which is a continuation of U.S. application Ser. No. 13/072,874 filed on Mar. 28, 2011 (now U.S. Pat. No. 8,277,435), which is a divisional of U.S. application Ser. No. 12/115,008 filed on May 5, 2008 (now U.S. Pat. No. 7,938,797), the entire contents of these previous applications are expressly incorporated herein by reference.

TECHNICAL FIELD

This disclosure relates to portable infusion pump systems to deliver fluids, such as insulin infusion pump systems or the like.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

SUMMARY

Some embodiments of a portable infusion pump system can be configured to can be configured to adjust the sensitivity of particular detectors or alert systems based (at least in part) on information received from a monitoring device. For example, a glucose monitoring device can communication with an infusion pump assembly used to supply insulin or another medication to a user. In such circumstances, the data received from the monitoring device can be used to adjust the sensitivity of an occlusion detection system or another alert system arranged in the infusion pump assembly. In one example, the infusion pump system can be configured increase the sensitivity of the occlusion detection system when the information from the glucose monitoring device indicates that that the user's blood glucose is greater than a normal range. As such, the occlusion detection system can more promptly alert the user to inspect the medicine delivery path for a possible clog or kink, thereby providing a timely remedy to the situation when insulin dispensation is an urgent concern (e.g., during the period of high blood glucose levels).

In particular embodiments, a medical infusion pump system may include a portable pump housing that receives a medicine for dispensation to a user. The pump housing may at least partially contain a pump drive system to dispense the insulin medicine through a flow path to the user. The system may also include a controller that activates the pump drive system to dispense the insulin medicine from the portable pump housing. The controller may operate an occlusion detection system that detects a fluid condition in the flow path. The occlusion detection system can have an adjustable sensitivity. The controller may output an occlusion alarm to the user when an occlusion is detected in the flow path. The system may further include a monitoring device that communicates glucose information to the controller. The glucose information may be indicative of a blood glucose level of the user. The sensitivity of the occlusion detection system can be adjusted in response to the glucose information received by the controller from the monitoring device.

Some embodiments may include a method of operating a medical infusion pump system. The method may include activating an occlusion detection system to detect a fluid condition in a flow path extending from a medicine reservoir in a portable pump assembly to user. The pump assembly may include a pump drive system to dispense medicine through the flow path to the user. The method may also include receiving glucose information from a monitoring device. The glucose information may be indicative of a detected blood glucose level of the user. The method may also include adjusting a sensitivity of the occlusion detection system in response to receiving the glucose information from the monitoring device. The method may also include outputting an occlusion alarm to the user when an occlusion is detected in the flow path.

Some or all of the embodiments described herein may provide one or more of the following advantages. First, some embodiments of an infusion pump system can include a monitoring device that interacts with an infusion pump assembly so as to delivery insulin or another medication while contemporaneously monitoring a user's blood characteristic. For example, the monitoring device can be configured to wireless communicate information indicative of the user's blood glucose level to the infusion pump assembly while the pump assembly operates to dispense the medication to the user.

Second, some embodiments of the pump assembly can be configured to adjust the sensitivity of particular detectors or alert systems based (at least in part) on information received from the monitoring device. For example, the infusion pump assembly can include an occlusion detection system with a controlled sensitivity, and the sensitivity of the occlusion detection system can be adjusted when the glucose information received from the monitoring device indicates that the user's glucose level is outside of a normal range. Such a feature can be useful when the user's blood glucose level is greater than a normal range, which creates an urgent concern for insulin dispensation and for prompt remedies to possible occlusions in the flow path.

Third, the infusion pump system can be configured to adjust the sensitivity of the occlusion detection system in a manner that decreases the likelihood of false alarms when blood glucose levels are in an acceptable range, while ensuring that the user is promptly alerted to possible occlusions when the blood glucose levels are dangerously high (e.g., at a time when insulin dispensation is an urgent concern). In particular circumstances, false alarms may be caused by transient kinks in the infusion set tubing that can self correct after a short period of time. If occlusion alarms are activated too frequently when such transient kinks are present (especially when blood glucose levels are detected within a normal range), the user may eventually choose to ignore or disable such occlusion alarms (believing them to be false alarms). Such a pattern could lead the user to mistakenly ignore authentic occlusion alarms and cause unsafe increases in blood glucose levels. As described in more detail below, the infusion pump system can employ a normal sensitivity setting for the occlusion detection system when blood glucose levels are in an acceptable range, thereby reducing the likelihood of false alarms during these periods of lower risk. However, the infusion pump system can employ a heightened sensitivity setting for the occlusion detection system when blood glucose levels are higher than a normal range, which can serve to promptly alert the user to possible occlusions at a time when insulin dispensation is an urgent concern.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a perspective view of the infusion pump system where the pump assembly of FIG. 1 is worn on clothing of a user.

FIG. 4 is a perspective view of an infusion pump system where the pump assembly is worn on skin of a user, in accordance with particular embodiments.

FIGS. 5-6 are perspective views of a pump device being detached from a controller device, in accordance with some embodiments.

FIGS. 13-16 are flow diagrams depicting exemplary processes used to determine whether adjustments are to be made to the sensitivity of an occlusion detection system based (at least in part) on glucose data, in accordance with some embodiments.

Like reference symbols in the various drawings indicate like elements.

DETAILED DESCRIPTION OF ILLUSTRATIVE EMBODIMENTS

Figure 1:
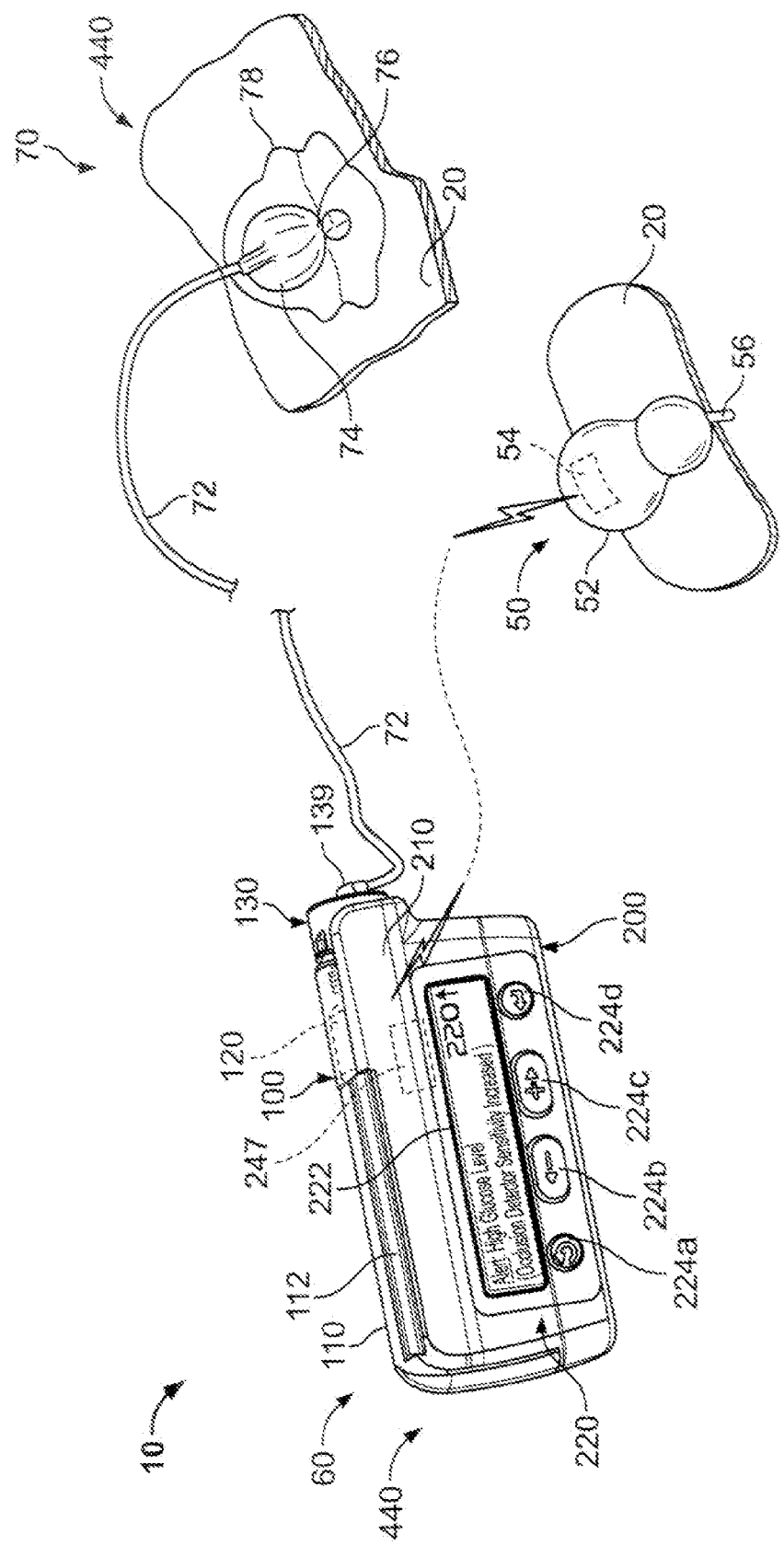
FIG. 1 is a perspective view of an infusion pump system including occlusion detection and glucose monitoring in accordance with some embodiments.

Referring to FIG. 1, an infusion pump system 10 can include a glucose monitoring device 50 in communication with an infusion pump assembly 60 used to supply insulin or other medication to a user via, for example, an infusion set 70. In some embodiments, the monitoring device 50 can be configured to supply information indicative of a user's blood glucose level to the infusion pump assembly 60. Based at least in part on the information supplied from the monitoring device 50 to the infusion pump assembly 60, the infusion pump assembly 60 can modify one or more processes associated with tasks performed by the infusion pump system 10. For example, in some embodiments, the pump assembly 60 can be configured to adjust the sensitivity of particular detectors or alert systems based (at least in part) on information received from the glucose monitoring device 50. In addition, or in the alternative, the pump assembly 60 can be configured to adjust the basal delivery rate, bolus dosages and timing, and/or other tasks performed by the pump assembly 60 based (at least in part) on information received from the glucose monitoring device 50.

In some embodiments, the glucose monitoring device 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In response to the measurements made by the sensor shaft 56, the glucose monitoring device 50 can employ the wireless communication device 54 to transmit data to controller device 200 of the pump assembly 60.

In some embodiments, the monitoring device 50 may include a circuit that permits sensor signals (e.g., data from the sensor shaft 56) to be communicated to the communication device 54. The communication device 54 can transfer the collected data to the infusion pump assembly 60 (e.g., by wireless communication to a communication device 247 arranged in the pump assembly 60). In some embodiments, the monitoring device 50 can employ other methods of obtaining information indicative of a user's blood characteristics and transferring that information to the infusion pump assembly 60. For example, an alternative monitoring device may employ a micropore system in which a laser porator creates tiny holes in the uppermost layer of a user's skin, through which interstitial glucose is measured using a patch. Alternatively, the monitoring device can use iontophoretic methods to non-invasively extract interstitial glucose for measurement. In other examples, the monitoring device can include non-invasive detection systems that employ near IR, ultrasound or spectroscopy and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some embodiments, the monitoring device 50 can be in communication with the pump assembly 60 via a wired connection. In some embodiments of the pump system 10, test strips (e.g., glucose test strips) containing a sample of the user's blood can be inserted into a portion of the pump assembly 60 to be tested for characteristics of the user's blood. Alternatively, the test strips (e.g., glucose test strips) containing a sample of the user's blood can be inserted into a glucose meter device, which then analyzes the characteristics of the user's blood and communicates the information (via a wired or wireless connection) to the pump assembly 60. In other embodiments, characteristics of the user's blood glucose information can be entered directly into the pump system 10 via a user interface on the controller device 200.

Figure 2:
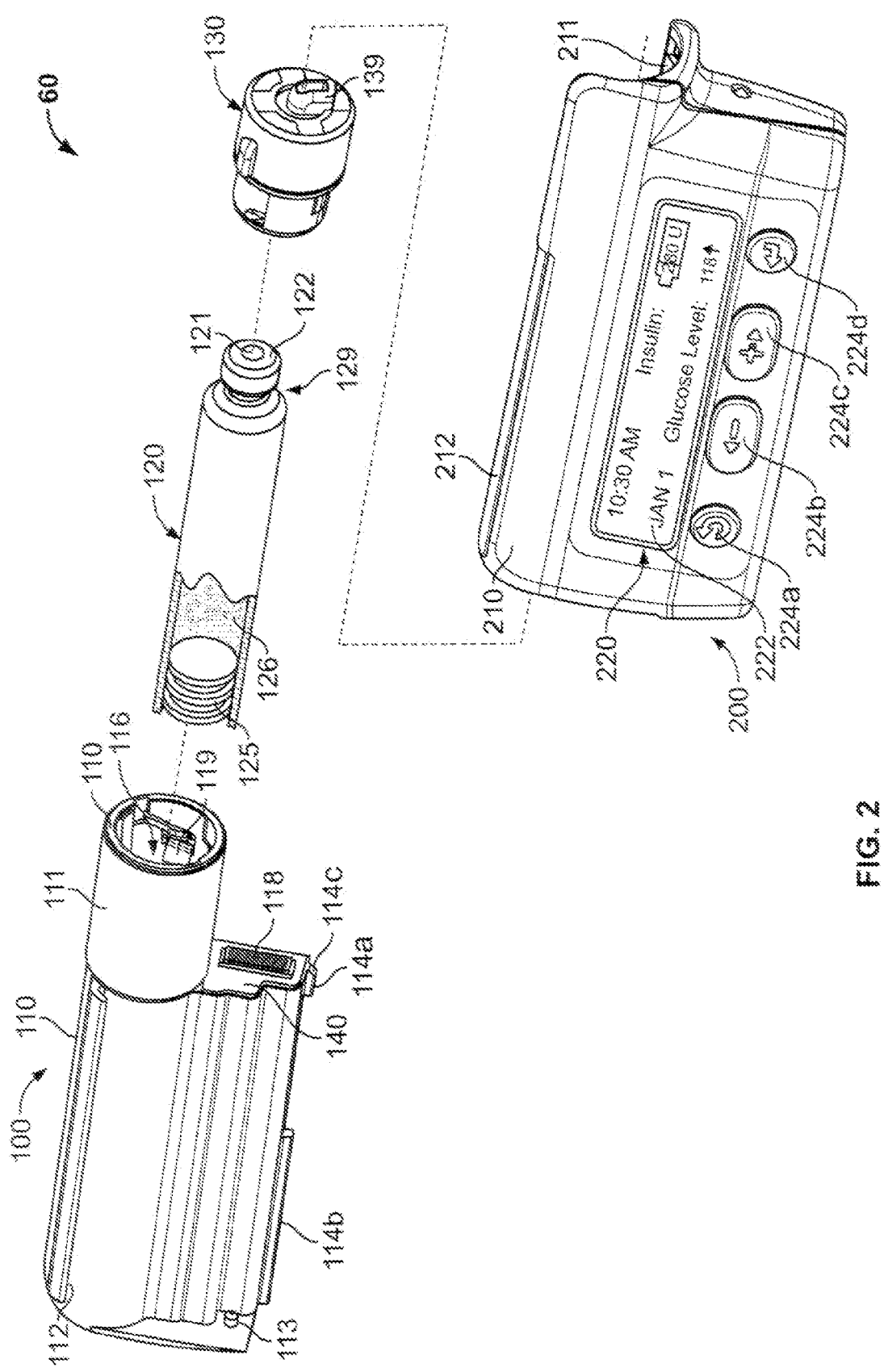
FIG. 2 is a perspective exploded view of the infusion pump assembly of FIG. 1.

Referring now to FIGS. 1-2, the infusion pump assembly 60 can include a pump device 100 and the controller device 200 that communicates with the pump device 100. The pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (described in more detail below) that advances a plunger 125 in the fluid cartridge 120 so as to dispense fluid therefrom. In some embodiments, the dispensed fluid exits the fluid cartridge 120, passes through a flexible tube 72 of the infusion set 70 to a cannula housing 74. The dispensed fluid can enter through the skin via a cannula 76 attached to the underside of the cannula housing 74.

In some embodiments, the controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump assembly 60 on the user's skin under clothing or in the user's pocket while receiving the fluid dispensed from the pump device 100.

The controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump assembly 60 can provide enhanced user safety as a new pump device 100 (and drive system therein) is employed with each new fluid cartridge 120.

Briefly, in use, the pump device 100 can be configured to removably attach to the controller device 200 in a manner that provides a secure fitting, an overall compact size, and a reliable electrical connection. In the example depicted in FIG. 1, the controller device 200 is removably attached with the pump device 100 in a generally side-by-side configuration while not fully surrounding the pump housing 110. Accordingly, the pump device 100 and the controller device 200 can be separate components that fit together, but the overall size of the combined assembly is reduced because there is no requirement for one component (e.g., the controller device) to completely surround or envelop the second component (e.g., the pump device). The compact size permits the infusion pump assembly 60 to be discrete and portable (as described below in more detail in connection with FIGS. 3-4). Moreover, at least one of the pump device 100 or the controller device 200 may include a release member that facilitates an easy-to-use detachment and replacement process. For example, as described in more detail below in connection with FIGS. 7-8, an exhausted pump device 100 may be a "one time use" component that is discarded after being used, and a new pump device 100' (having a new medicine cartridge 120') can thereafter be attached to the controller device 200.

Moreover, the pump device 100 and the controller device 200 can be mounted to one another so that the assembled pump assembly 60 is resistant to migration of external contaminants (e.g., water from precipitation or splashing, sweat, and the like) into the pump device 100 or the controller device 200. In particular, the infusion pump assembly 60 may include one or more seals that are arranged to hinder migration of external contaminants into the cavity of the pump device 100 (e.g., to protect the insulin container 120 and the drive system during operation). Also, the infusion pump assembly 60 may include one or more gaskets arranged proximate to the electrical connection location (between the pump device 100 and the controller device 200) to protect the electrical connection from external contaminants. Thus, in some embodiments, the infusion pump system 10 can be assembled into a water resistant configuration that protects sensitive components from water migration (e.g., if the user encounters water while wearing the pump assembly 60).

As described in more detail below, the pump assembly 60 can include a sensor configuration that detects occlusions in the fluid flow path extending to the user. In the embodiment depicted in FIGS. 1-2, the fluid flow path can include the delivery from the medicine cartridge 120, through the cap 130, and through the infusion set 70. For example, the controller device 200 can communicate with a pressure sensor 380 (refer to FIG. 10) arranged in the pump device 100 so as to detect high pressures created by occlusions. In another example, the controller device 200 may include an optical sensor system 250 (refer to FIGS. 17-19) that detects the amount of light reflected from a portion of the cap device 130. The optical sensor system 250 may include a number of components that are housed in the controller device 200. In one example, the light emitter and light sensor may be arranged on a sensor circuit in the controller device 200, thereby permitting these components to be reused along with the controller device (while the relatively low cost components in the pump device 100 are discarded after the "one time use" of the pump device 100).

It should be understood that, in alternative embodiments, the pump device 100 and the controller device 200 can be configured as a single unit in which the control components and the pump drive system are arranged in a single housing. In these alternative embodiments, the pump assembly (including the controller device and the pump device) may have a different size and shape and may operate as a reusable unit that can communicate with a number of monitoring devices 50 over a period of time.

Referring again to FIGS. 1-2, in some embodiments, the pump system 10 is a medical infusion pump system that is configured to controllably dispense a medicine from the cartridge 120. As such, the fluid cartridge 120 may contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others).

Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the pump device 100 may include one or more structures that interfere with the removal of the medicine cartridge 120 after the medicine cartridge 120 is inserted into the cavity 116. For example, as shown in FIG. 2, the pump housing structure 110 may include one or more retainer wings 119 that at least partially extend into the cavity 116 to engage a portion of the medicine cartridge 120 when the medicine cartridge 120 is installed therein. In this embodiment, the pump housing structure 110 includes a pair of opposing retainer wings 119 (only one is shown in the view in FIG. 2) that flex toward the inner surface of the cavity 116 during insertion of the medicine cartridge 120. After the medicine cartridge is inserted to a particular depth, the retainer wings 119 are biased to flex outward (toward the center of the cavity 116) so that the retainer wings 119 engage a neck portion 129 of the medicine cartridge 120. This engagement with the retainer wings 119 and the neck portion 129 hinder any attempts to remove the medicine cartridge 120 away from the pump device 100. Alternative embodiments can include other features and/or configurations to hinder the removal of the medicine cartridge 120.

Embodiments of the pump device 100 that hinder the removal of the medicine cartridge 120 may facilitate the "one-time-use" feature of the pump device 100. Because the retainer wings 119 can interfere with attempts to remove the medicine cartridge 120 from the pump device 100, the pump device 100 will be discarded along with the medicine cartridge 120 after the medicine cartridge 120 is emptied, expired, or otherwise exhausted. The retainer wings 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-2, the cap device 130 can be joined with the pump device 100 after the medicine cartridge is inserted in the cavity 116. It should be understood that the cap device 130 may supplement or replace the previously described retainer wings 119 by locking into position after joining with the pump housing 110, thereby hindering removal of the fluid cartridge 120 in the pump housing 110. As shown in FIGS. 1-2, the cap device 130 may include an output port 139 that connects with the tubing 72 for dispensation of the medicine to the user. In some embodiments, the output port 139 may have an angled orientation such that a portion of the tubing extends transversely to the central axis of the cartridge 120 and cap device 130. The output port 139 can be configured to mate with tubing 72 of the infusion set 70 (FIG. 1).

Still referring to FIGS. 1-2, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (described in connection with FIG. 10) of the pump device 100. As described in more detail below, the pump device 100 includes a drive system that causes controlled dispensation of the medicine or other fluid from the cartridge 120. In some embodiments, the drive system incrementally advances a piston rod longitudinally into the cartridge 120 so that the fluid is forced out of an output end 122. The septum 121 at the output end 122 of the fluid cartridge 120 can be pierced to permit fluid outflow when the cap device 130 is connected to the pump housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

In some embodiments, the controller device is configured to removably attach to the pump device 100 in a side-by-side arrangement. The compact size permits the infusion pump assembly 60 to be discrete and portable when the pump device 100 is attached with the controller device 200 (as shown in FIG. 1). In this embodiment, the controller device 200 includes a controller housing structure 210 having a number of features that are configured to mate with complementary features of the pump housing structure 110 so as to form a releasable mechanical connection (described below in more detail in connection with FIGS. 5-8). Such mating features of the pump housing structure 110 and the controller housing structure 210 can provide a secure connection in the previously described side-by-side arrangement As shown in FIG. 2, the pump device 100 may include an electrical connector 118 (e.g., having conductive pads, pins, or the like) that are exposed to the controller device 200 and that mate with a complementary electrical connector (refer to connector 218 in FIG. 6) on the adjacent face of the controller device 200. The electrical connectors 118 and 218 provide the electrical communication between the control circuitry (refer, for example, to FIG. 9) housed in the controller device 200 and at least a portion of the drive system or other components of the pump device 100. In some exemplary embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump assembly 60 may include a gasket 140 that provides a seal which is resistant to migration of external contaminants when the pump device 100 is attached to the controller device 200. Thus, in some embodiments, the pump device 100 and the controller device 200 can be assembled into a water resistant configuration that protects the electrical interconnection from water migration (e.g., if the user encounters water while carrying the pump assembly 60).

Still referring to FIGS. 1-2, the controller device 200 includes a user interface 220 that permits a user to monitor the operation of the pump device 100. In some embodiments, the user interface 220 includes a display 222 and one or more user-selectable buttons (e.g., four buttons 224a, 224b, 224c, and 224d in this embodiment). The display 222 may include an active area in which numerals, text, symbols, images, or a combination thereof can be displayed (refer, for example, to FIG. 2). For example, the display 222 may be used to communicate a number of alarms, settings, and/or menu options for the infusion pump system 10. In some embodiments, the display 222 can indicate the user's blood glucose level, an indication that the user's blood glucose level is rising or falling, and if adjustments have been made to the sensitivity of an occlusion detection system. For example, FIG. 1 depicts an embodiment in which the display 222 alerts the user that the detected blood glucose level is at 220 mg/dL, the blood glucose level is rising (as communicated by the upward facing arrow), and that the sensitivity of the occlusion detector has been adjusted due to the blood glucose data detected by the monitoring device 50.

In some embodiments, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time.

The display 222 of the user interface 220 may be configured to display quick reference information when no buttons 224a, 224b, 224c, and 224d have been pressed. For example, as shown in FIG. 2, the active area of the display 222 can display the time, date, insulin remaining in medicine cartridge 120, blood glucose level, and an indication of whether the user's blood glucose level is rising or falling. This information can be displayed for a period of time after no button 224a, 224b, 224c, and 224d has been actuated (e.g., five seconds, 10 seconds, 30 seconds, 1 minute, 5 minutes, or the like). Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 22 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the display 222 of the controller device 200. Such monitoring capabilities may provide comfort to a user who may have urgent questions about the current operation of the pump device 100 (e.g., the user may be unable to receive immediate answers if wearing an infusion pump device having no user interface attached thereto).

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200 without the requirement of locating and operating a separate monitoring module.

In other embodiments, the user interface 200 is not limited to the display and buttons depicted in FIGS. 1-2. For example, in some embodiments, the user interface 220 may include only one button or may include a greater numbers of buttons, such as two buttons three buttons, four buttons, five buttons, or more. In another example, the user interface 220 of the controller device 200 may include a touch screen so that a user may select buttons defined by the active area of the touch screen display. Alternatively, the user interface 220 may comprise audio inputs or outputs so that a user can monitor the operation of the pump device 100.

Referring to FIGS. 3-4, the infusion pump system 10 may be configured to be portable and can be wearable and concealable. For example, a user can conveniently wear the infusion pump assembly 60 on the user's skin (e.g., skin adhesive) underneath the user's clothing or carry the pump assembly 60 in the user's pocket (or other portable location) while receiving the medicine dispensed from the pump device 100. The pump device 100 may be arranged in a compact manner so that the pump device 100 has a reduced length. For example, in the circumstances in which the medicine cartridge 120 has a length of about 7 cm or less, about 6 cm to about 7 cm, and about 6.4 cm in one embodiment, the overall length of the pump housing structure 110 (which contains medicine cartridge and the drive system) can be about 10 cm or less, about 7 cm to about 9 cm, and about 8.3 cm in one embodiment. In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump assembly 60 (including the removable controller device 200 attached to the pump device 100 having the cap 130) may have an overall length of about 11 cm or less, about 7 cm to about 10 cm, and about 9.6 cm in one embodiment; an overall height of about 6 cm or less, about 2 cm to about 5 cm, and about 4.3 cm in one embodiment; and an overall thickness of about 20 mm or less, about 8 mm to about 20 mm, and about 18.3 mm in one embodiment.

The pump system 10 is shown in FIGS. 3-4 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 may be configured to mate with the infusion set 70. In general, the infusion set 70 is tubing system that connects the infusion pump system 10 to the tissue or vasculature of the user (e.g., to deliver medicine into the tissue or vasculature under the user's skin). The infusion set 70 may include the flexible tube 72 that extends from the pump device 100 to the subcutaneous cannula 76 retained by a skin adhesive patch 78 that secures the subcutaneous cannula 76 to the infusion site. The skin adhesive patch 78 can retain the infusion cannula 76 in fluid communication with the tissue or vasculature of the patient so that the medicine dispensed through the tube 72 passes through the cannula 76 and into the user's body. The cap device 130 may provide fluid communication between the output end 122 (FIG. 2) of the medicine cartridge 120 and the tube 72 of the infusion set 70. For example, the tube 72 may be directly connected to the output port 139 (FIG. 2) of the cap device 130. In another example, the infusion set 70 may include a connector (e.g., a Luer connector or the like) attached to the tube 72, and the connector can then mate with the cap device 130 to provide the fluid communication to the tube 72. In these examples, the user can carry the portable infusion pump assembly 60 (e.g., in the user's pocket, connected to a belt clip, adhered to the user's skin, or the like) while the tube 72 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

Referring to FIG. 3, in some embodiments, the infusion pump assembly 60 is pocket-sized so that the pump device 100 and controller device 200 can be worn in the user's pocket 6 or in another portion of the user's clothing. For example, the pump device 100 and the controller device 200 can be attached together and form the assembly 60 that comfortably fits into a user's pocket 6. The user can carry the portable infusion pump assembly 60 and use the tube 72 of the infusion set 70 to direct the dispensed medicine to the desired infusion site. In some circumstances, the user may desire to wear the pump assembly 60 in a more discrete manner. Accordingly, the user may pass the tube 72 from the pocket 6, under the user's clothing, and to the infusion site where the adhesive patch 78 is positioned. As such, the pump system 10 can be used to deliver medicine to the tissues or vasculature of the user in a portable, concealable, and discrete manner. Furthermore, the monitoring device 50 can be worn on the user's skin while the pump assembly 60 is carried by the user (e.g., in a pocket). As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

Referring to FIG. 4, in other embodiments, the infusion pump assembly 60 may be configured to adhere to the user's skin 7 directly at the location in which the skin is penetrated for medicine infusion. For example, a rear surface of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 76 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220. Furthermore, the monitoring device 50 can be worn on the user's skin while the pump assembly 60 is worn on the user's skin in a different location from that where the monitoring device is worn. As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

In the embodiments depicted in FIGS. 3-4, the monitoring device 50 adheres to the user's skin 7 at the location in which the skin is penetrated by the sensor shaft 56 (to detect blood glucose levels). The sensor shaft 56 (refer to FIG. 1) penetrates the skin surface for the purpose of exposing the tip portion of the sensor shaft 56 to the tissue or the vasculature of the user. The sensor shaft 56 can detect information indicative of the user's blood glucose level and transfer this information to a circuit that is connected to the communications device 54 located within the monitoring device 50. The communication device 54 can be in wireless communication with the communication device 247 (described in connection with FIG. 9) included in the controller 200 of the pump assembly 60.

Referring now to FIGS. 5-8, in some embodiments, the infusion pump assembly 60 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 (FIG. 2) is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 5-6, the pump device 100 can be readily removed from the controller device 200 when the medicine cartridge 120 is exhausted. As previously described, the medicine cartridge 120 is arranged in the cavity 116 (FIG. 2) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length.

As shown in FIG. 5, the pump device 100 has been used to a point at which the medicine cartridge 120 is exhausted. The plunger 125 has been advanced, toward the left in FIG. 5, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 to determine if the medicine cartridge 120 is almost empty. When the user determines that a new medicine cartridge 120 should be employed, the pump device 100 can be readily separated from the controller device 200 by actuating a release member 215. In this embodiment, the release member 215 is a latch on the controller device 200 that is biased toward a locking position to engage the pump device 100. The latch may be arranged to engage one or more features on a lateral side of the pump housing 110. As such, the user may actuate the release member 215 by moving the release member 215 in a lateral direction 216 (FIG. 5) away from the pump device 100 (e.g., by applying a force with the user's finger).

As shown in FIG. 6, when the release member 215 is actuated and moved to a position away from the pump device 100, a segmented guide rail 114a-b is free to slide longitudinally in a guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 2) may be withdrawn from the mating depression 213 (FIG. 6), and the electrical connector 118 can be separated from the mating connector 218. In these circumstances, the pump device 100 is physically and electrically disconnected from the controller device 200 while the pump device retains the exhausted medicine cartridge 120. It should be understood that, in other embodiments, other features or connector devices can be used to facilitate the side-by-side mounting arrangement. These other features or connector devices may include, for example, magnetic attachment devices, mating tongues and grooves, or the like.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., moved in the lateral direction 216 in the embodiment shown in FIG. 5). Accordingly, in some embodiments, the pump device 100 can automatically and sharply move a small distance (e.g., about 0.5 mm to about 5 mm) away from the controller 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Figure 7:
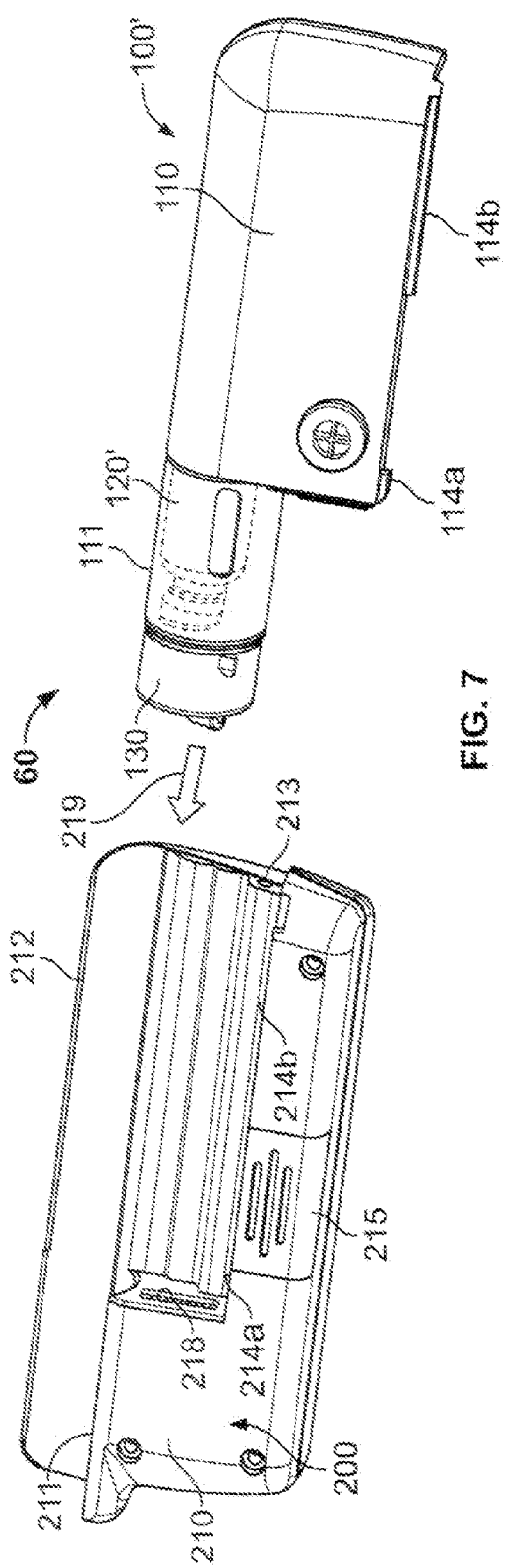
FIGS. 7-8 are perspective views of the pump device of FIGS. 5-6 being discarded and the controller device of FIGS. 5-6 being reused with a new pump device.
Figure 8:
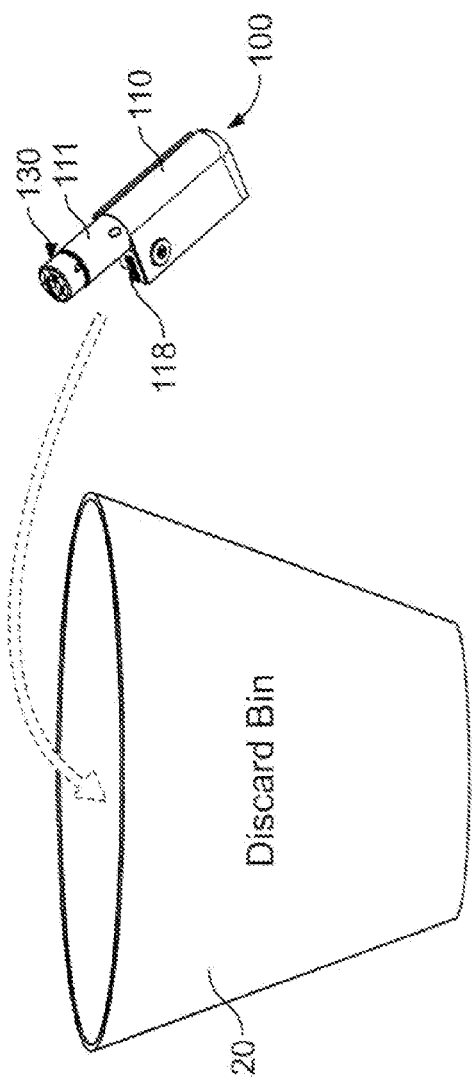

Referring to FIGS. 7-8, the same controller device 200 can be reused with a new pump device 100' having a new medicine cartridge 120' retained therein, and the previously used pump device 100 can be discarded with the exhausted medicine cartridge 120. The new pump device 100' (FIG. 7) can have a similar appearance, form factor, and operation as the previously used pump device 100 (FIGS. 5-6), and thus the new pump device 100' can be readily attached to the controller device 200 for controlled dispensation of medicine from the new medicine cartridge 120'. In some embodiments, the user may prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 2). Although the tubing 72 of the infusion set 70 is not shown in FIG. 7, it should be understood that the tubing 72 may be attached to the cap device 130 prior to the cap device 130 being joined with the housing 110. For example, a new infusion set 70 can be connected to the cap device 130 so that the tubing 72 can be primed (e.g., a selected function of the pump device 100 controlled by the controller 200) before attaching the infusion set patch to the user's skin. As shown in FIG. 7, the new medicine cartridge 120' may be filled with medicine such that the plunger 125 is not viewable through the barrel 111. In some embodiments, the user can removably attach the pump device 100 to the controller 200 by moving the pump device 100 in a longitudinal direction 219 toward the controller device 200 such that the segmented guide rail 114a-b engages and slides within the guide channel 214a-b. When the electrical connectors 118 and 218 mate with one another, the release member 215 can engage the segmented guide rails 114a-b to retain the pump device 100 with the controller device 200.

As shown in FIG. 8, the previously used pump device 100 that was separated from the controller device (as described in connection with FIGS. 5-6) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 30, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 70 (not shown in FIG. 8, refer to FIG. 1) that was used with the pump device 100 may be removed from the user and discarded into the bin 30 along with the pump device 100. Alternatively, the infusion set 70 can be disconnected from the previous pump device 100 and attached to the new pump device 100'. In these circumstances, the user may detach the infusion set cannula 76 and patch 78 from the skin so as to "re-prime" the tubing with medicine from the new pump device 100' to remove air pockets from the tubing. Thereafter, the infusion set cannula 76 and patch 78 can be again secured to the user's skin.

Figure 9:
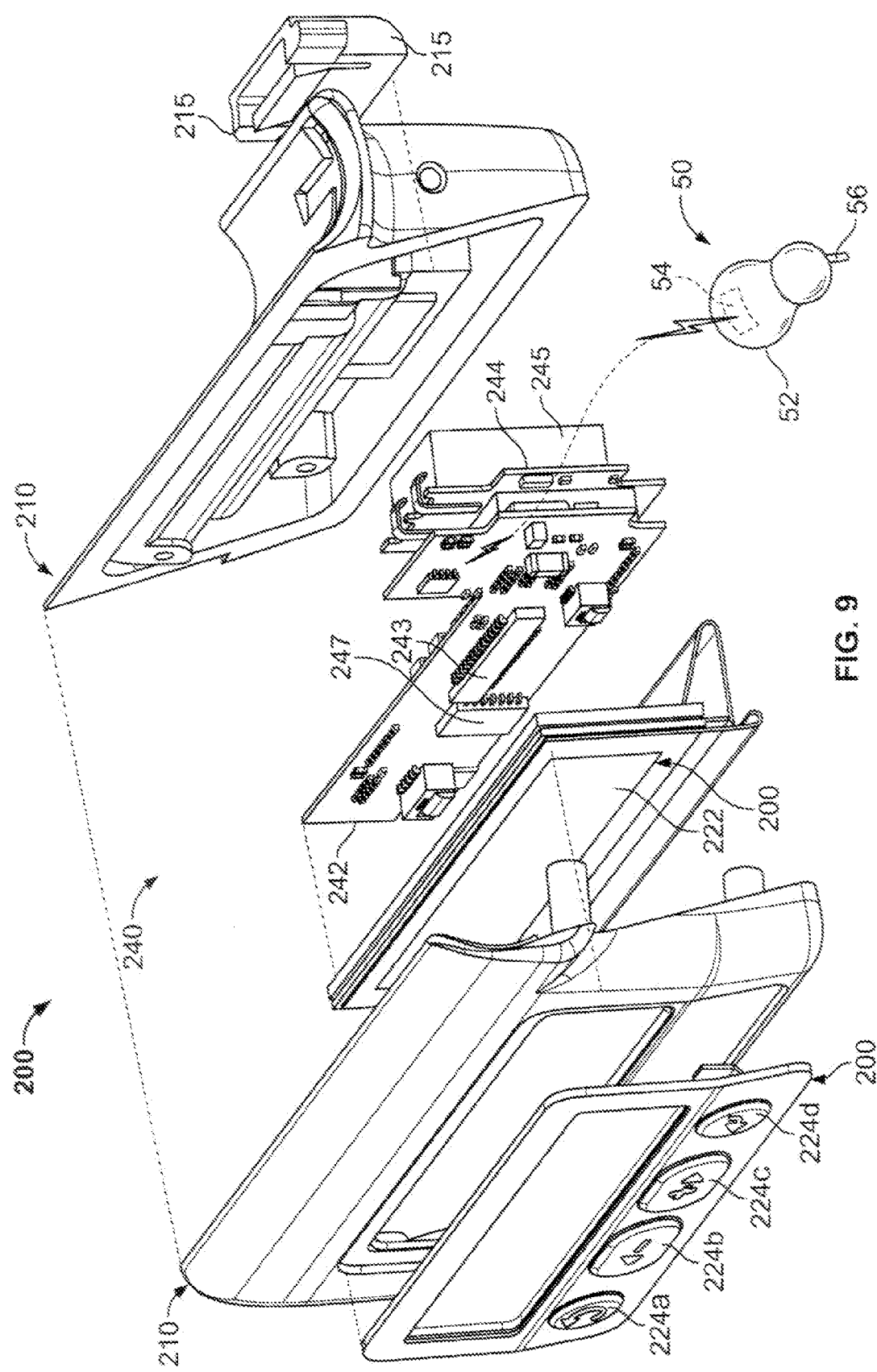
FIG. 9 is an exploded perspective view of a controller device for an infusion pump system, in accordance with some embodiments.

Referring now to FIG. 9, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices. It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the memory devices arranged in the control circuitry 240. Furthermore, the control circuitry 240 may include one or more dedicated memory devices that store executable software instructions for the processor 243. The control circuitry 240 may include other components, such as sensors, that are electrically connected to the main processor board 242. For example, in some embodiments, at least a portion of an occlusion detection system 250 can be electrically connected to the main processor board 242 via a flexible circuit substrate or one or more wires, as described in more detail below in connection with FIGS. 17-19.

As previously described, the controller device 200 can be electrically connected with the pump device 100 via mating connectors 118 and 218 so that the control circuitry 240 can communicate control signals to the pump device 100 and receive feedback signals from components housed in the pump device 100. In this embodiment, the electrical connector 118 (FIG. 2) on the pump device 100 is a z-axis connector, and the connector 218 (FIG. 6) on the controller device 200 is adapted to mate therewith. The electrical connector 218 on the controller device 200 is in communication with the control circuitry 240. As such, the processor 243 can operate according to software instructions stored in the memory device so as to send control signals to the pump device 100 via the connector 218.

Still referring to FIG. 9, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of settings or menu options for the infusion pump system 10. In this embodiment, the control circuitry 240 may receive the input commands from the user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port, another data cable port, or a data cable connection via the electrical connection 218) that is accessible on an external portion of the controller housing 210. As such, a cable may be connected to the control circuitry 240 to upload data or program settings to the controller circuit or to download data from the control circuitry 240. For example, historical data of medicine delivery can be downloaded from the control circuitry 240 (via the cable connector) to a computer system of a physician or a user for purposes of analysis and program adjustments. Optionally, the data cable may also provide recharging power.

Figure 10:
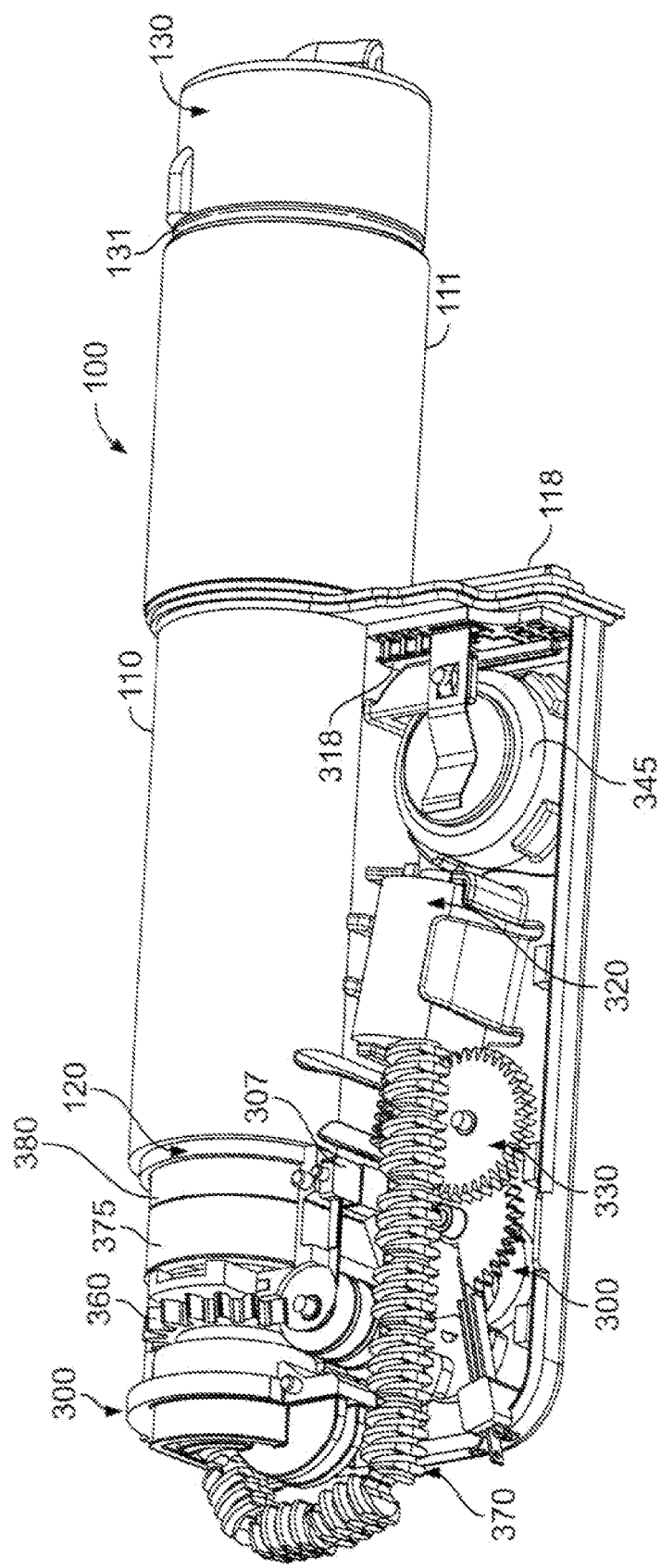
FIG. 10 is a perspective view of a portion of a pump device for an infusion pump system, in accordance with particular embodiments.

Referring to FIGS. 9-10, the control circuitry 240 of the controller device 200 may include a second power source 245 (FIG. 9) that can receive electrical energy from a first power source 345 (FIG. 10) housed in the pump device 100. In this embodiment, the second power source 245 is coupled to the power supply board 244 of the control circuitry 240. The hard-wired transmission of the electrical energy can occur through the previously described connectors 118 and 218. In such circumstances, the first power source 345 may include a high density battery that is capable of providing a relatively large amount of electrical energy for its package size, while the second power source 245 may include a high current-output battery that is capable discharging a brief current burst to power the drive system 300 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, the first battery 345 may comprise a zinc-air cell battery. The zinc-air cell battery 345 may have a large volumetric energy density compared to some other battery types. Also, the zinc-air cell battery may have a long storage life, especially in those embodiments in which the battery is sealed (e.g., by a removable seal tab or the like) during storage and before activation.

The second battery 245 may include a high current-output device that is housed inside the controller housing 210. The second battery 245 can be charged over a period of time by the first battery 345 and then intermittently deliver high-current bursts to the drive system 300 over a brief moment of time. For example, the second battery 245 may comprise a lithium-polymer battery. The lithium polymer battery disposed in the controller device 200 may have an initial current output that is greater than the zinc-air cell battery disposed in the pump device 100, but zinc-air cell battery may have an energy density that is greater than the lithium polymer battery. In addition, the lithium-polymer battery 245 is readily rechargeable, which permits the zinc-air battery 345 disposed in the pump device 100 to provide electrical energy to the lithium-polymer battery 245 for purposes of recharging. In alternative embodiments, it should be understood that the second power source 245 may comprise a capacitor device capable of being recharged over time and intermittently discharging a current burst to activate the drive system 105.

Accordingly, the infusion pump system 10 having two power sources 345 and 245—one arranged in the pump device 100 and another arranged in the reusable controller device 200—permits a user to continually operate the controller device 200 without having to recharge a battery via a wall-plug or other cable. Because the controller device 200 can be reusable with a number of pump devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Referring now to FIG. 10, the pump device 100 in this embodiment includes the drive system 300 that is controlled by the removable controller device 200 (see FIG. 2). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. Some embodiments of the drive system 300 may include a battery powered actuator (e.g., reversible motor 320 or the like) that actuates a gear system 330 to reset a ratchet mechanism (e.g., including a ratchet wheel and pawl), a spring device (not shown) that provides the driving force to incrementally advance the ratchet mechanism, and a drive wheel 360 that is rotated by the ratchet mechanism to advance the flexible piston rod 370 toward the medicine cartridge 120. Connected to piston rod 370 is a pusher disc 375 for moving the plunger 125 of the medicine cartridge 120.

Some embodiments of the drive system 300 can include a pressure sensor 380 disposed between the plunger engagement device 375 and the plunger 125 for determining the pressure within the fluid path (e.g., inside the medicine cartridge 120, the infusion set 70, and the like). For example, the fluid pressure in the medicine cartridge 120 can act upon the plunger 125, which in turn act upon the pressure sensor 380 arranged on the dry side of the plunger 125. The pressure sensor 380 may comprise a pressure transducer that is electrically connected (via one or more wires) to a gateway circuit 318 so that the sensor signals can be communicated to the controller device 200 (e.g., via the electrical connectors 118 and 218). As such, data from the pressure sensor 380 can be received by the controller device 200 for use with an occlusion detection module to determines if an occlusion exists in the medicine flow path.

Figure 11A:
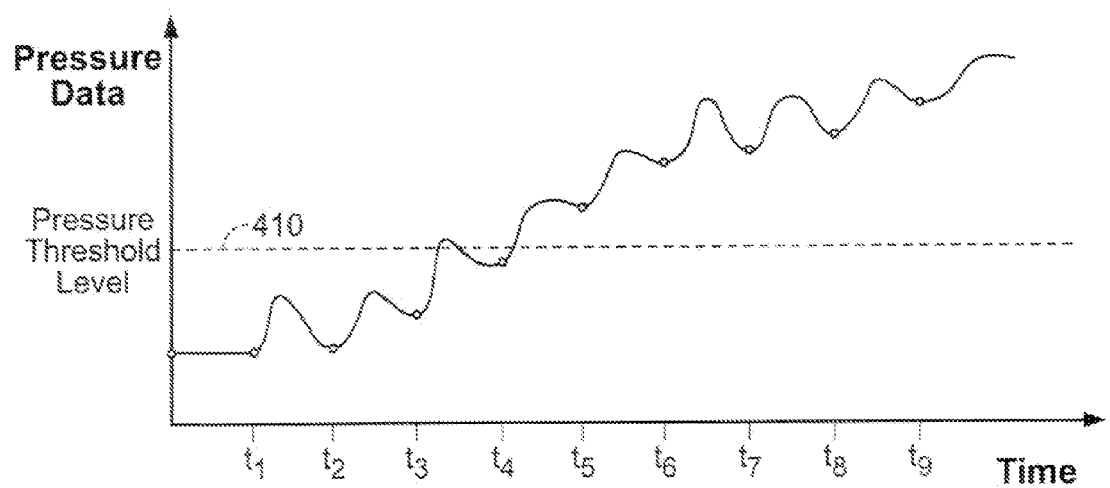
FIG. 11A is a diagram depicting a fluid pressure curve as measured by a pressure sensor, in accordance with some embodiments.

The pressure within the medicine cartridge 120 may change over time and may be characterized by a pressure curve such as the example depicted by FIG. 11A. As described above in connection with FIG. 10, activation of the drive system 300 results in the plunger 125 being incrementally advanced within the medicine cartridge 120. This advancement of the plunger 125 (FIG. 2) causes an initial increase in pressure inside the fluid path which, under normal conditions (e.g., when no occlusion is present), causes a controlled amount of fluid to be delivered out of the cartridge 120 and to the user. In some embodiments, the pressure sensor 380 samples the pressure within the medicine cartridge 120 at a time immediately before the activation of the drive system 300. FIG. 11A represents nine such activations of the drive system 300 and the coincident sampling of the pressure at the times labeled $t_1$-$t_9$. The period from $t_0$-$t_1$ represents a time period when the drive system 300 is idle, the pressure within the medicine cartridge 120 is at an equilibrium, and no fluid is being dispensed from the pump assembly 60.

At time $t_1$ (just before the drive system 300 is activated), the pump assembly 60 samples the fluid pressure (e.g., using the pressure sensor 380) and communicates the detected pressure to the controller device 200. The time between $t_1$ and $t_2$ represents an example of a generally normal pump activation cycle where the drive system 300 advances an incremental amount, causing the plunger to move within the medicine cartridge 120 and the pressure to increase within the fluid path. As fluid is expelled from the medicine cartridge 120, the pressure generally returns to the equilibrium value.

Still referring to FIG. 11A, at time $t_2$ (just before the drive system 300 is activated again), the pressure sensor 380 samples the fluid pressure in the cartridge 120. In this example, the sensor data indicates that the fluid pressure returned generally to the equilibrium level, thereby indicating that the incremental dosage from the previous activation cycle was properly expelled from the cartridge 120 and into the user's body.

In this pump activation cycle (i.e., the time between $t_2$ and $t_3$), the expected amount of fluid is not expelled from the medicine cartridge 120 due to an occlusion in the in the medicine flow path (e.g., a kink in the infusion set tube 72, a blockage in the flow path, or the like). At time $t_3$, the pressure is sampled and the pressure sensor 380 indicates that the pressure within the medicine cartridge 120 has not returned to the equilibrium value (e.g., the pressure value depicted between times $t_0$ and $t_1$), but the detected pressure is also not greater than a predetermined pressure threshold level 410. On activation of the drive system 300 after $t_3$, the pressure increases due to the advancement of the plunger 125 to a level that is greater than the threshold level 410. After advancement of the plunger 125, the pressure falls due to partial delivery of a dosage (e.g., some of the fluid is not delivered from the medicine cartridge 120 to the user due to a kink or partial blockage). For example, the detected pressure does not return to the level measured at $t_3$ or the equilibrium value seen in the time interval between $t_0$ and $t_1$. At time $t_5$, the pressure sampled is above the threshold level 410 for the first time in this example. In this embodiment, the controller device 200 does not necessarily provide an alarm upon the first pressure detection above the threshold pressure 410. Instead, in some embodiments, the controller device 200 may provide the alarm only after a pattern of high pressure detections have occurred (e.g., so as to avoid instances of false alarms that can be a nuisance to the user). Continuing with this example in FIG. 11A, during the next four subsequent activations of the drive system 300 (e.g., at $t_6$-$t_9$) the sampled pressure values are all above the threshold value 410. As described below in connection with FIG. 12, the controller device 200 may use these consecutive high pressure measurements to determine that an occlusion exists and alert the user (e.g., occlusion alarm).

Figure 11B:
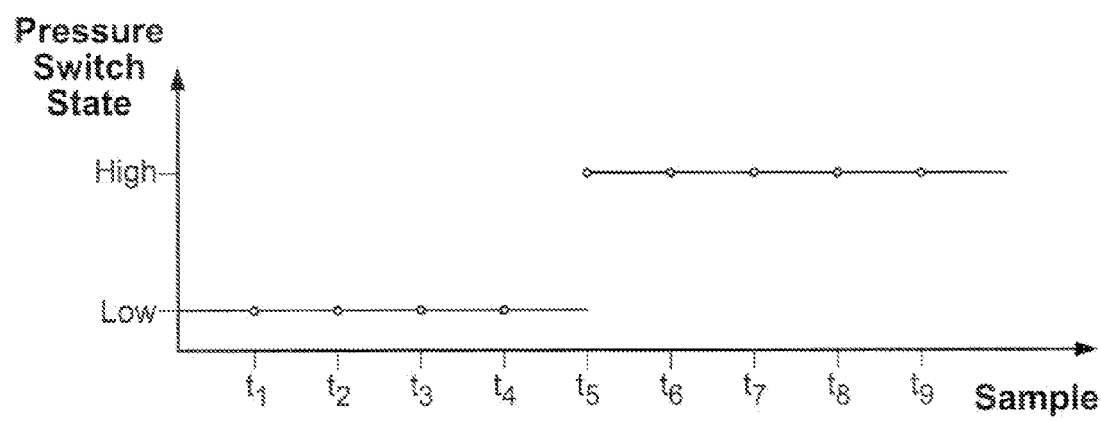
FIG. 11B is a diagram depicting the output of a pressure switch when measuring a pressure curve as similar to that depicted in FIG. 11B, in accordance with some embodiments.

Referring now to FIG. 11B, the pump assembly 60 can include the pressure sensor 380 that operates as a pressure switch to output "high" or "low" signals. For example, the pressure sensor 380 may not output a signal indicative of the actual pressure magnitude within the medicine cartridge 120, but instead may communicate either a "high" or a "low" signal depending on the detected pressure within the medicine cartridge 120. When the pressure detected by the sensor 380 is greater than a predetermined value, the sensor 380 communicates the "high" signal. When the pressure is lower than the predetermined value, the sensor 380 communicates the "low" signal.

FIG. 11B depicts an exemplary output of the pressure swith in the case where the actual pressure magnitude within the medicine cartridge 120 is the same as the pressure within the medicine cartridge 120 depicted in FIG. 11A. As in the example depicted by FIG. 11A, the pressure sensor 380 is sampled immediately before the activation of the drive system 300. In this example, the predetermined pressure threshold that marks the boundary between high and low signals is the same pressure threshold value 410 from FIG. 11A. When the pressure on the pressure sensor 380 is greater than the pressure threshold value 410, the pressure sensor 380 communicates a "high" signal. Conversely, when the pressure on the pressure sensing disc is less than or equal to the pressure threshold value 410, the pressure sensor 380 communicates a "low" signal.

As seen in FIG. 11A, when the pressure sensor 380 is sampled at times $t_1$-$t_4$, the actual pressure magnitude in the medicine cartridge 120 is less than pressure threshold 410. Since the actual pressure magnitude is less than the pressure threshold 410, the pressure sensor 380 as configured in the example associated with FIG. 11B communicates a "low" signal to the controller device 200. At sampling time $t_5$, the pressure is greater than the threshold 410 causing the sensor 380 to output a "high" signal to the controller device 200. Subsequent sampling times $t_6$-$t_9$ coincide with pressures that are greater than the threshold 410, causing the sensor 380 to output a "high" signal. As previously described, the controller device 200 does not necessarily provide an alarm upon the first "high" signal received from the pressure sensor 380. In some circumstances, the controller device 200 may use a pattern of consecutive "high" signals to determine that an occlusion exists. As described below, the sensitivity of the occlusion detection system may be adjusted based upon changes to this pattern.

In some embodiments, the infusion pump system 10 is configured to alert the user when an occlusion is detected so as to remedy the possible interruption of medicine delivery to the user. In certain situations, it may be advantageous to detect a pattern of high pressure signals (e.g., as illustrated in FIG. 11A or 11B) before communicating the alert the user. For example, transient kinks can occur in the flexible tube 72, but these types kinks can self correct after a period of time. During the period of this transient kink, the pressure within the medicine cartridge 120 can rise above a predetermined threshold (e.g., the pressure threshold level 410), but it is possible that the kink can subsequently self correct after a short period of time (thereby allowing the fluid to dispense to the user without any occlusion alarms that require intervention from the user).

If occlusion alarms are activated too frequently when such transient kinks are present (especially when blood glucose levels fall within a normal range), the user may eventually choose to ignore or disable such occlusion alarms (believing them to be false alarms). Such a pattern may lead the user to ignore authentic occlusion alarms and cause unsafe increases in blood glucose levels. If occlusion alarms are activated only after too long of a period of high pressure detections, the user may experience substantial increases in blood glucose levels due to the flow path occlusion. To provide a suitable balance to these factors, the infusion pump system 10 can include an occlusion detection system with an adjustable sensitivity value. The sensitivity value can be used to decrease the likelihood of false alarms when blood glucose levels are in an acceptable range, while ensuring that the user is promptly alerted to possible occlusions when the blood glucose levels are dangerously high (e.g., at a time when insulin dispensation is an urgent concern).

In one embodiment, the adjustable sensitivity values can be indicative of a time period (e.g., 2 minutes, 5 minutes, 10 minutes, or the like) to momentarily delay a user alarm after detecting a high pressure magnitude in the fluid path. In these examples, the controller device 200 can identify a high pressure detection indicative of an occlusion and wait a predetermined period of time before alerting the user of this condition. If the occlusion is corrected (either with or without user intervention) within the period of time, the occlusion alarm can be cancelled. In these examples, if an occlusion is corrected within a period of time, the user may never be alerted that the transient occlusion existed, thus minimizing the amount of false alarms communicated to the user.

In other embodiments, the sensitivity value can include a number (e.g., 1, 2, 3, 4, 5, 6, or the like) indicating the quantity of times that the pressure sensor 380 consecutively outputs a high pressure signal (e.g., above a pressure threshold value 410) before alerting the user. For example, the controller device 200 may be programmed with a sensitivity value of "5", indicating that five consecutive pressure samples must be greater than the pressure threshold level 410 before an occlusion is determined to exist. In the examples depicted in FIGS. 11A-11B, the first occurrence of a pressure sample that is greater than the pressure threshold 410 occurs at time $t_5$. In this case, if the sensitivity value is set to "5", the user will not be alerted to the occlusion until after the sample taken at time $t_9$. If, between sampling times $t_5$ and $t_9$, the occlusion is corrected (either with or without user intervention), the occlusion alert will not be communicated to the user, thereby minimizing the amount of false alarms received by the user.

Figure 12:
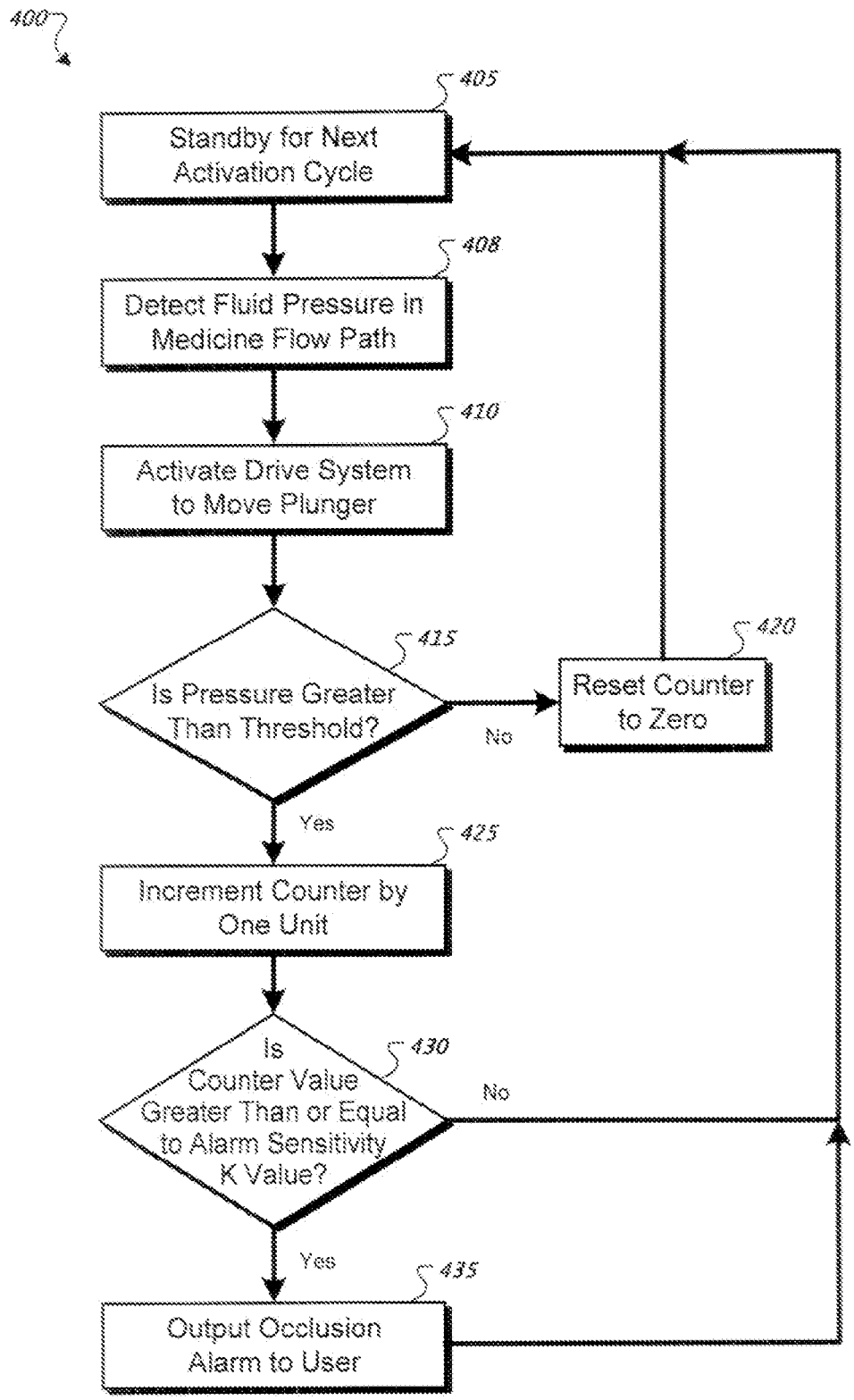
FIG. 12 is a flow diagram depicting an exemplary process used to determine when a user should be alerted to an occlusion, in accordance with some embodiments.

Referring now to FIG. 12, some embodiments of a process 400 for outputting an occlusion alarm to a user can include a number of operations performed by the controller device 200. In operation 405, the controller device 200 is in a standby mode in which the pump assembly 60 is awaiting the next activation cycle of the drive system 300. In operation 408, the pressure fluid is detected. For example, as previously described, the pump assembly 60 may include the pressure sensor 380 (FIG. 10) that outputs a sensor signal indicative of the pressure magnitude in the fluid path to the controller device 200. In operation 410, the drive system 300 is activated. For example, the controller device 200 may activate the drive system 300 to deliver an incremental dosage of medicine in accordance with the basal delivery program. As previously described, activation of the drive system 300 causes the plunger 125 to advance within the medicine cartridge 120 (FIG. 2). Advancing the plunger 125 causes the pressure inside the fluid path (e.g., the medicine cartridge 120, the infusion set 70, and the like) to increase thus expelling fluid out the output port 139, through the flexible tube 72, out the cannula 76, and into the user through the skin. As the fluid is expelled, the pressure within the medicine cartridge returns to an equilibrium pressure, at which point fluid is no longer delivered from the medicine cartridge 120. In the case of an occlusion (e.g., a kink in the flexible tube 72, a blockage in the cannula 76, or the like) the advancing plunger 125 may cause an increase in the fluid pressure because the pressure created within the medicine cartridge 120 during the advancing of the plunger 125 may not be fully relieved by the incremental dispensation of fluid to the user.

In operation 415, the pressure value obtained during operation 408 is compared to a predetermined threshold value. (It should be understood that operation 415 may occur before, after, or contemporaneously with the operation 410 so long as it occurs after operation 408.) If the sampled pressure is less than or equal to the threshold pressure, operation 420 is performed and a counter value is reset to zero. The counter value may be, for example, a numerical value stored in memory of the controller device 200. Thereafter, the process 400 may return to operation 405 in which the controller 200 returns to the standby mode.

If operation 415 indicates that the sampled pressure is greater than the pressure threshold, operation 425 is performed to incrementally increase the counter. After the counter is incremented during operation 425, operation 430 is performed, comparing the value stored in the counter to a predetermined alarm sensitivity K value. If the counter is less than the sensitivity K value, the process 400 returns to operation 405. If the counter is greater than or equal to the sensitivity K value, operation 435 is performed and the controller device 200 outputs an occlusion alarm to the user. The occlusion alarm may include a message on the display 222 (refer, for example, to FIG. 1), an audible alert, or another alert to communicate with the user.

As previously described, the infusion pump system 10 can be configured to adjust sensitivity value based (at least in part) on the information received from the glucose monitoring device. In some embodiments, the sensitivity K value may be selected so that the occlusion alarm is provided to the user in a timely manner while reducing the likelihood of false alarms. If a user's blood glucose level is high, the risk posed by an occlusion may be significant. As such, the sensitivity of the occlusion detection system may be increased during periods when the monitoring device 50 indicates that the user's blood glucose level is within a designated "high" range (refer, for example, to FIG. 13). However, if a user's blood glucose level falls within a "normal" range, the problems associated with false alarms (e.g., false alarms may be a nuisance for the user) may be greater than the need for rapid or immediate occlusion alarms. As such, the sensitivity of the occlusion detection system may be returned to a standard setting (e.g., moderate sensitivity) when the monitoring device 50 indicates that the user's blood glucose level is within a "normal" range.

Accordingly, the pump system 10 can be configured to adjust the sensitivity of the occlusion detection system based (at least in part) on the detected blood glucose level or another blood characteristic. Such adjustments can be used to decrease the likelihood of false alarms when blood glucose levels are in an acceptable range, while ensuring that the user is promptly alerted to possible occlusions when the blood glucose levels are high and insulin dispensation is an urgent concern.

Referring to FIG. 13, some embodiments of a process 500 can be utilized to adjust the sensitivity of an occlusion detection system based (at least in part) on information indicative of a blood glucose level. The process 500 may include a number of operations that are performed by the controller device 200 of the pump system 10. In operation 505, the controller device 200 may receive glucose data from, for example, the monitoring device 50. As previously described, the monitoring device 50 may communicate wirelessly with the controller device 200. In operation 510, the controller device 200 can compare the glucose level obtained during operation 505 to a predetermined threshold value. If the user's sensed glucose level is not greater than a threshold value (e.g., a glucose level representing an upper limit of a normal range), the process 500 can return to operation 505 and stands by for subsequent glucose monitoring data.

If the glucose level is greater than the threshold value, operation 515 is performed and the sensitivity of the occlusion detection system is increased. In some embodiments, the controller device 200 increases the sensitivity of the occlusion detection system by decreasing the sensitivity K value (described in connection with FIG. 12). In one example, the sensitivity K value can be decreased from "5" to "3", meaning that only three consecutive high pressure detections are required to activate the occlusion alarm (instead of five). As such, the user is more promptly alerted to possible occlusions when the blood glucose levels are higher than the normal range.

In some circumstances, the pump system 10 may indicate to the user that the detected glucose level (e.g., as detected by the glucose monitoring device 50) is at an elevated state. In operation 520, the controller 200 can provide an alert to the user indicating that the user's glucose level is elevated (refer, for example, to FIG. 1). Also, in some embodiments, the pump system 10 may indicate to the user that the sensitivity of the occlusion detection system was adjusted. For example, in operation 525, the controller device 200 can provide an alert to the user indicating that the sensitivity of the occlusion detection system has been increased. After completion of operation 525, process 500 can return to operation 505 and receive additional information that is indicative of the user's blood glucose level. It should be understood that, after the user's blood glucose levels have returned to a normal range, the sensitivity of the occlusion detection system may likewise return to a previous value condition (in this example, the sensitivity K value can be returned to "5", meaning that five or more consecutive high pressure detections are required to activate the occlusion alarm).

In some embodiments, it may be advantageous for the pump system 10 to modify the sensitivity of an occlusion detection system based (at least in part) on something other than the measured glucose level of the patient (refer to FIG. 13). For example, a user's glucose level may be within a normal range but increasing at a high rate, which may indicate that the user's glucose level could soon be above an upper limit of a normal range. In some circumstances, the pump system 10 can adjust the sensitivity of the occlusion detection system in response to a high rate of change in the detected glucose level. As such, the system can respond to a significant rate of increase in the blood glucose level without necessarily waiting for the blood glucose level to rise to a high value. In one example, a current glucose measurement indicates that a user's blood glucose level is 185 mg/dL and the controller 200 is programmed with a normal range of 80-200 mg/dL. If a previous glucose measurement (e.g., taken 10 minutes before the current measurement) may have indicated a blood glucose level of 165 mg/dL for the user. In this case, the user's blood glucose level has risen at a rate of 20 mg/dL in 10 minutes. At this rate of increase, the blood glucose level could soon be above the upper limit of the normal range, representing a dangerous condition for the user that could be exacerbated by an occlusion in the fluid delivery path of the pump system 100. In this example, it may be advantageous for the controller device 200 to recognize the high rate at which the blood glucose level is rising and increase the sensitivity of the occlusion detection system for the safety of the user.

In one example, referring to FIG. 14, a process 600 can be utilized to adjust the sensitivity of the occlusion detection system. A number of operations in the process 600 can be performed by the controller device 200. For example, in operation 605, the controller device 200 can receive glucose data from the monitoring device 50 so as to determine the rate at which the glucose level is rising (e.g., by comparing the current value with one or more previous values). In operation 610, the controller device 200 can compare the rate at which the measured glucose level is rising to a predetermined threshold rate value. In the example in which the measured glucose level is not rising at a rate that is greater than the threshold rate value, the process 600 can return to operation 605 and await further glucose data. If the measured glucose level, as determined by the controller 200, is rising at a rate that is greater than the threshold rate value, operation 615 is performed to increase the sensitivity of the occlusion detection system. In some embodiments, operation 615 can be performed by the controller device 200 to increase the sensitivity of the occlusion detection system by decreasing the alarm sensitivity K value described in connection with FIG. 12. In one example, the sensitivity K value is decreased from "5" to "3", meaning that only three consecutive high pressure detections are required to activate the occlusion alarm (instead of five).

In these embodiments, the pump system 10 may indicate to the user (e.g., via the display device 222, an audible tone, or the like) that the user's blood glucose level is changing at a high rate and/or that the sensitivity of the occlusion detection system was adjusted. For example, in operation 620, the controller device 200 can provide an alert to the user indicating that the user's glucose level is rising at an elevated rate. In operation 625, the controller device 200 can provide an alert to the user indicating that the sensitivity of the occlusion detection system has been increased (refer, for example, to FIG. 1). It should be understood that, after the user's blood glucose level ceases rising at an elevated rate and is maintained within a normal range, the sensitivity of the occlusion detection system may return to a previous value condition (in this example, the sensitivity K value can be returned to "5", meaning that five or more consecutive high pressure detections are required to activate the occlusion alarm).

In some embodiments, the sensitivity of the occlusion detection system can be adjusted if the user's blood glucose level falls below a normal range. For example, if a user's blood glucose level falls below a safe level, the need to consume food and raise the blood glucose level may be more urgent than with receiving more insulin and/or responding to possible occlusions alarms. In such circumstances, the sensitivity of the occlusion detection may be decreased to temporarily reduce the instances of possible false alarms, which may become a nuisance and distract the user from increasing the blood glucose level.

Figure 15:
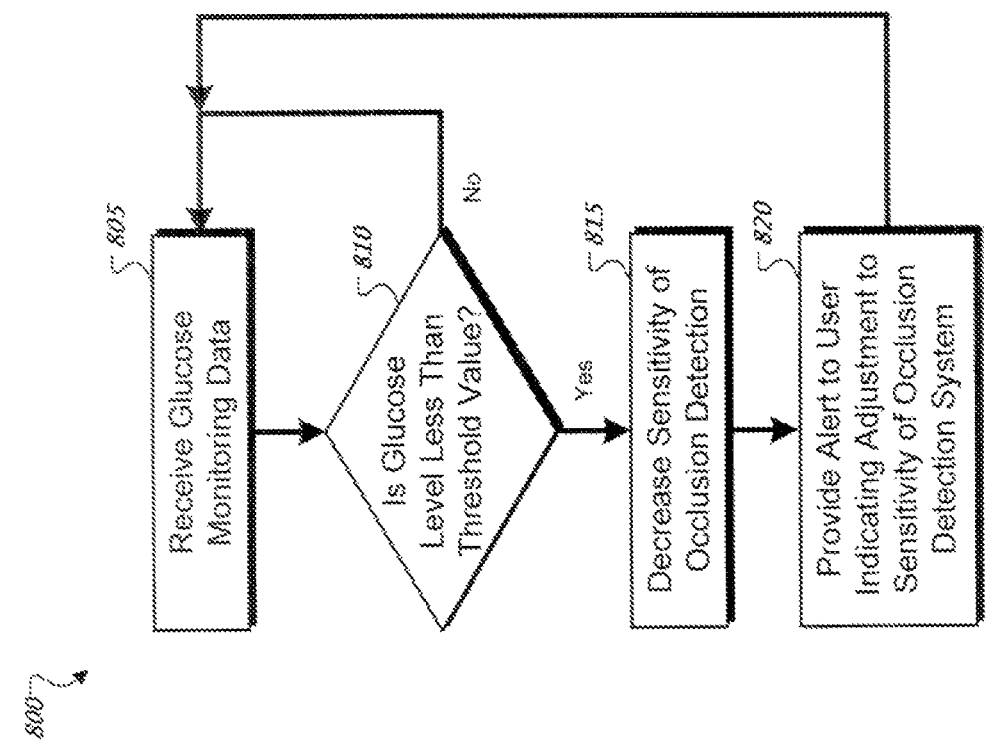

Referring to FIG. 15, a process 800 can be utilized to decrease the sensitivity of an occlusion detection system based (at least in part) on the glucose information transmitted from the monitoring device. The process 800 may include a number of operations that are performed by the controller device 200 of the pump system 10. In operation 805, the controller 200 may receive glucose data from the monitoring device 50 via, for example, wireless communication. In operation 810, the controller 200 may compare the measured glucose level obtained during operation 805 to a predetermined minimum threshold value (e.g., a glucose level representing a lower limit of a normal glucose range). If the measured glucose level is not less than the threshold value, the process 800 returns to operation 805 and stands by for subsequent glucose monitoring data. If the measured glucose level is less than the threshold value, operation 815 is performed and the controller device 200 may decrease the sensitivity of the occlusion detection system (e.g., to reduce the occurrence of false alarms, nuisance alarms, or the like). In some embodiments, the controller device 200 decreases the sensitivity of the occlusion detection system by increasing the alarm sensitivity K value (described in connection with FIG. 12). In one example, the sensitivity K value is increased from "5" to "7", meaning that seven consecutive high pressure detections are required to activate the occlusion alarm (instead of five), before outputting an alarm to the user.

Similar to previously described embodiments, the pump system 10 may indicate to the user that the sensitivity of the occlusion detection system was adjusted. For example, in operation 820, the controller device 200 can provide an alert to the user indicating that the sensitivity of the occlusion detection system has been decreased (e.g., via the display device 222, an audible tone, or the like). The controller device 200 may contemporaneously alert the user of the detected glucose level that is lower than the normal range. After completion of operation 820, process 800 can return to operation 805 and stands by for subsequent glucose data. It should be understood that, after the user's blood glucose level returns to the normal range, the sensitivity of the occlusion detection system may likewise return to a previous value condition (in this example, the sensitivity K value can be returned to "5", meaning that five or more consecutive high pressure detections are required to activate the occlusion alarm).

In some embodiments, it may be advantageous for the pump system 10 to modify the sensitivity of an occlusion detection system based (at least in part) on a significant rate of decrease of the user's blood glucose level. For example, a user's glucose level may be within a normal range, but decreasing at a high rate, indicating that the user's glucose level could soon fall below a lower limit of a normal range. In some embodiments, the pump system 10 can adjust the sensitivity of the occlusion detection system in response to the negative rate of change in the detected glucose level. As such, the system can respond to a significant rate of decrease in the blood glucose level without necessarily waiting for the blood glucose level to fall below the normal range. In this example, the controller device 200 can recognize the significant rate at which the blood glucose level is falling and decrease the sensitivity of the occlusion detection system so as to temporarily reduce the instances of possible false alarms, which may become a nuisance and distract the user from maintaining normal glucose levels.

Figure 16:
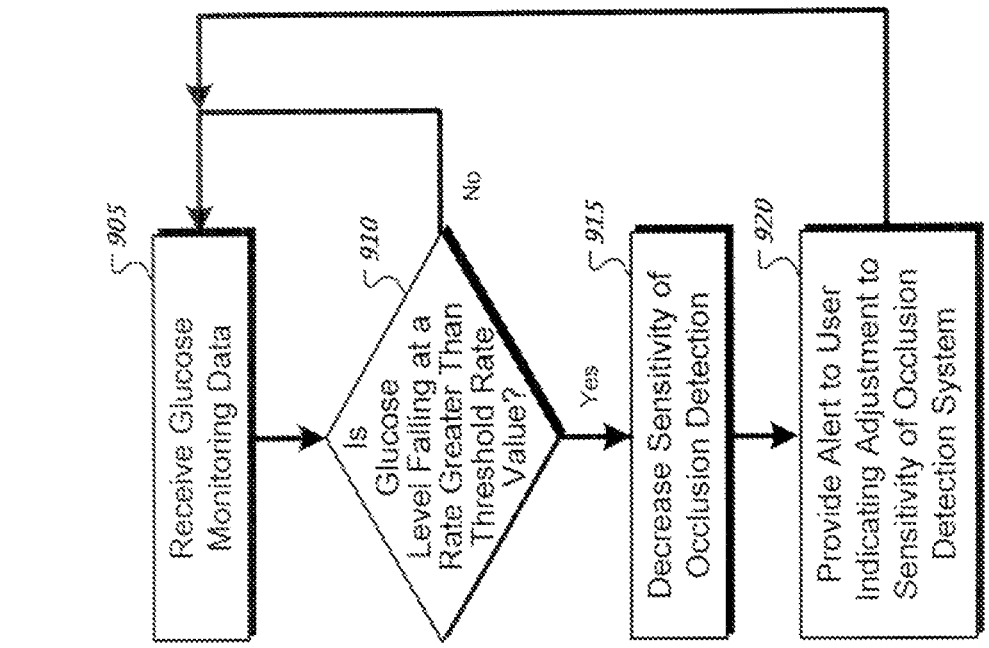

Referring to FIG. 16, in one example, a process 900 can be utilized to adjust the sensitivity of an occlusion detection system. A number of operations in the process 900 can be performed by the controller device 200. For example, in operation 905, the controller device 200 can receive glucose data from, for example, the monitoring device 50 so as to determine the rate at which the glucose level is falling (e.g., by comparing the recent value to one or more previous values). In operation 910, the controller device 200 can compare the rate at which the measured glucose level is falling to a predetermined threshold rate value. If the measured glucose level is not falling at a rate that is greater than the threshold rate value, the process 900 returns to operation 905 and stands by for subsequent glucose monitoring data. If the measured glucose level is falling at a rate greater than the threshold rate value, operation 915 is performed to decrease the sensitivity of the occlusion detection system. In some embodiments, the sensitivity of the occlusion detection system is decreased by the controller 200, in operation 915, by increasing the alarm sensitivity K value (as described in connection with FIG. 12). In one example, the sensitivity K value is increased from "5" to "7", meaning that seven consecutive high detections are required to activate the occlusion alarm (instead of five).

Similar to previously described embodiments, the pump system 10 may indicate to the user (e.g., via the display device 222, an audible tone, or the like) that the sensitivity of the occlusion detection system was adjusted. For example, in operation 920, the controller device 200 can provide an alert to the user indicating that the sensitivity of the occlusion detection system has been decreased. The controller device 200 may also alert the user of the detected glucose level is decreasing at a significant rate. After completion of operation 920, process 900 can return to operation 905 and stands by for subsequent glucose data. It should be understood that, after the user's blood glucose level is no longer decreasing at a significant rate and is maintained within the normal range, the sensitivity of the occlusion detection system may return to a previous value condition (in this example, the sensitivity K value can be returned to "5", meaning that five or more consecutive high pressure detections are required to activate the occlusion alarm).

In alternate embodiments, the process for adjusting the sensitivity of an occlusion detection system can include multiple threshold values (or rate values) that can cause stepped adjustments to the sensitivity of the occlusion detection system. For example, a first threshold value can be employed to cause adjustment of the sensitivity K value (refer to FIG. 12) from "5" to "4" when the detected blood glucose level reaches past the first threshold value, while a second threshold value can be employed to cause adjustment of the sensitivity K value from "4" to "3" when the detected blood glucose level reaches past the second threshold value. Additional threshold values may be employed to further adjust the sensitivity K value. In other embodiments, the baseline sensitivity K value can be selected to be a value other than five (e.g., "2", "3", "4", "6", "7", or the like).

Figure 17:
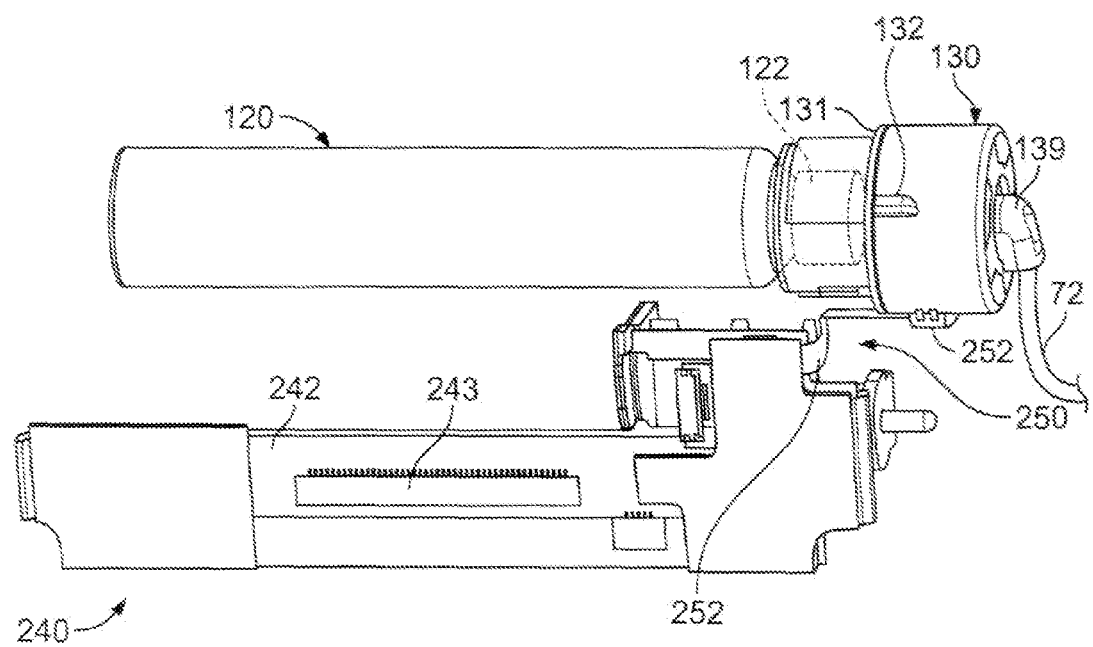
FIG. 17 is a perspective view of occlusion sensor circuitry for an optical occlusion detection system, in accordance with some embodiments.
Figure 18:
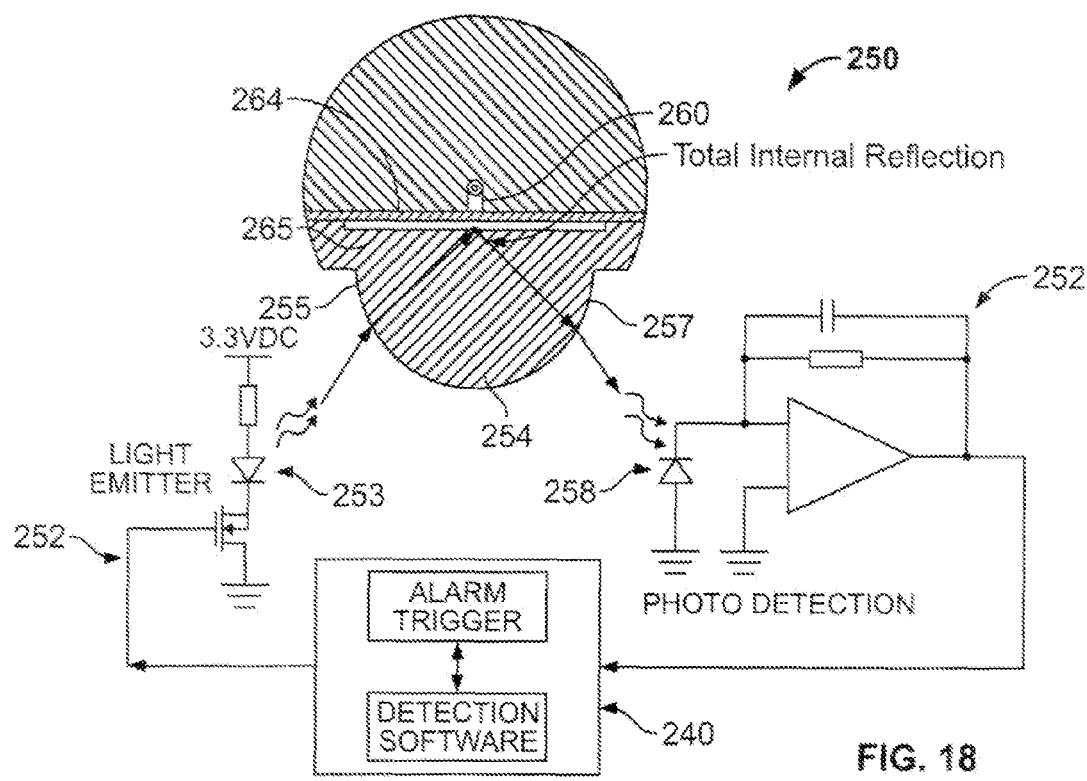
FIGS. 18-19 are diagrams of the occlusion sensor of FIG. 17.
Figure 19:
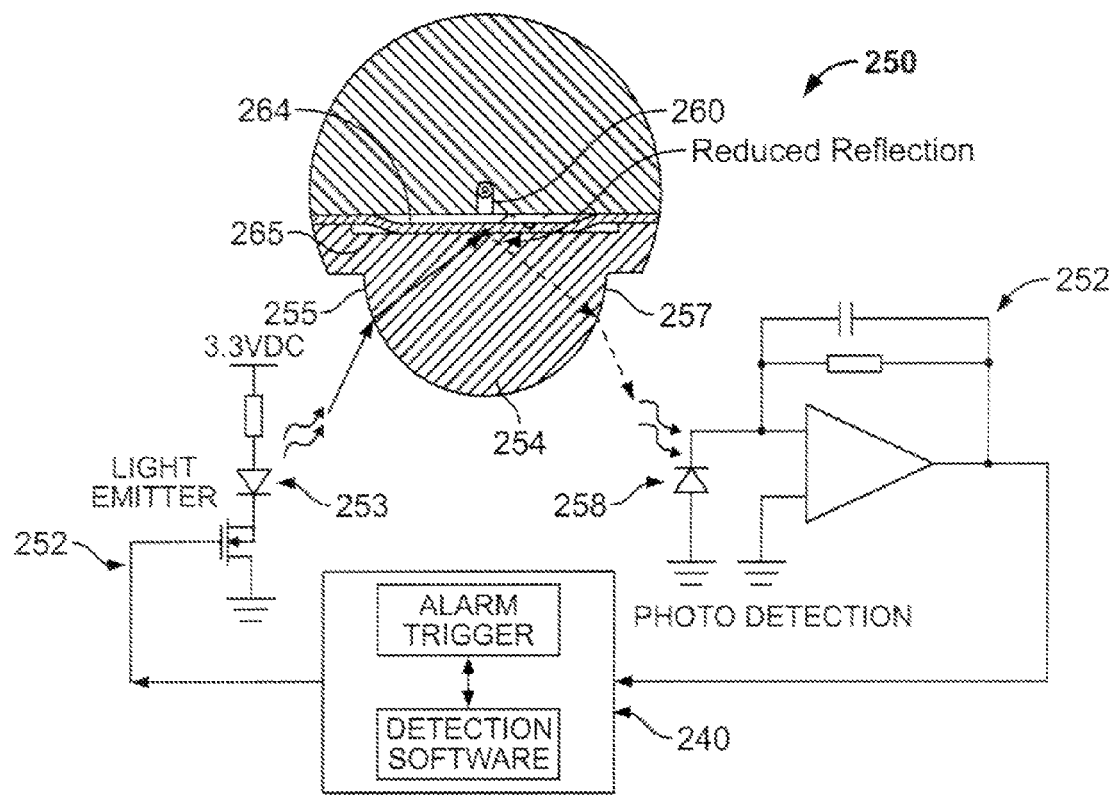

Referring now to FIGS. 17-19, the occlusion detection system is not limited to embodiments that employ a pressure transducer or a pressure switch. For example, the infusion pump system 10 can be equipped with an optical occlusion detection system 250. In some embodiments, the controller device 200 may include the optical sensor detection system 250 to detect the amount of light reflected from a portion of the cap device 130 or another portion of the medicine flow path. The optical detection system 250 can detect changes in the amount of light reflected from the cap device 130 in response to an occlusion that causes an increase in the fluid pressure in the medicine flow path. For example, as described below in connection with FIGS. 18-19, the optical sensor system 250 may operate using the principle of total internal reflection.

Referring to FIG. 17, although the optical sensor system 250 operates to detect changes in the flow path from the pump device 100 (e.g., through the cap device 130), the optical sensor system 250 may include a number of components that are housed in the controller device 200. For example, a light emitter and light sensor may be arranged on a sensor circuit 252 that is housed by the controller device 200, thereby permitting these components to be reused along with the controller device (while the relatively low cost components in the pump device 100 are discarded after the "one time use" of the pump device 100). The sensor circuit 252 can be arranged so that the cap device 130 is aligned with the light emitter and the light sensor (described below) when the pump device 100 is attached to the controller device 200. It should be understood that the pump housing 110 and the controller housing 210 have been removed from FIG. 17 for purposes of showing the relative position of the sensor circuit 252 and the cap device 130 (attached to the pump housing 110 as shown in FIG. 2).

The sensor circuit 252 can be connected to the control circuitry 240 of the controller device 200 (see FIG. 9 for the location of the control circuitry 240 within the controller 200) via a flexible circuit substrate or one or more wires. In this embodiment, the sensor circuit 252 connects with the main processor board 242 via a flexible circuit substrate. The control circuitry 240 can receive sensor signals and employ detection software stored in one or more memory devices to determine if an occlusion exists. As described in more detail below, if the sensor signals from optical sensor system 250 indicate that an occlusion exists in the fluid flow path, the controller device 200 can trigger an alert to inform the user. The alert may include a visual or audible alarm communicated via the user interface 220 of the controller device 200.

Referring now to FIGS. 18-19, in some embodiments, the controller device 200 can determine whether an occlusion exists using sensor signals communicated to the control circuitry 240 of the controller device 200. In particular, the control circuitry 240 can be used to activate the light emitter 253 and the light sensor 258 at selected times to monitor the fluid pressure in the flow path. For example, the control circuitry 240 can activate the light emitter 253 and the light sensor 258 one or more times during activation of the drive system 300 (FIG. 10) to force medicine from the medicine cartridge 120, before the drive system 300 is activated, or after the drive system 300 is activated. The control circuitry 240 can receive detector signals from the light sensor 258 and thereafter process the data to determine if an alert should be triggered to notify the user of an occlusion.

Referring to FIG. 18, in this embodiment, the control circuitry 240 can activate the sensor circuit 252 one or more times shortly after the drive system 300 (FIG. 10) is activated (e.g., while the drive system 300 is operating) to force medicine from the medicine cartridge 120. When the sensor circuit 252 is activated, the light emitter 253 emits light toward the internal light transmissive member 254, passing through a first curved surface 255. The light from the light emitter 253 can be in the form of an infrared light beam. As shown in FIG. 18, when no substantial occlusion exists in the flow path, the fluid pressure of the medicine passing through the cap device 130 may be below a selected threshold value. In these circumstances, the flexible membrane 264 that is adjacent to the fluid channel 260 is not substantially deformed (e.g., the membrane 264 does not flex downwardly into the air cavity 265 to abut the internal light transmissive member 254). The light from the light emitter 253 can be reflected at the interface where the internal light transmissive member 254 meets the air cavity 265. In some embodiments, this light reflection may occur due to total internal reflection at the interface. This reflected light continues through the internal light transmissive member 254 toward a second curved surface 257. The second curved surface 257 may operate as a focusing lens that directs the infrared light toward the light sensor 258. As previously described, in some embodiments, the light sensor 258 may comprise an infrared photo detector that is capable of converting the receipt of infrared light into electrical signals. These electrical signals from the light sensor 258 can be transmitted via the sensor circuit 252 to the control circuitry 240. The control circuitry 240 receives the signals from the light sensor 258 and uses this data, along with additional information such as the alarm sensitivity K value described in connection with FIG. 12, to determine if an occlusion alarm should be provided to the user. In the example depicted in FIG. 18, the control circuitry 240 receives signals that indicate the pressure in the fluid channel 260 is within the normal operating range.

Referring to FIG. 19, the control circuitry 240 can again activate the sensor circuit 252 one or more times shortly before the drive system 300 (FIGS. 18-20) is activated to force medicine from the medicine cartridge 120. When the sensor circuit 252 is activated, the light emitter 253 emits light toward the light transmissive member 254. When an occlusion exists in the flow path, the fluid pressure of the medicine passing through the cap device 130 may rise to a level above the threshold value. For example, when one or more earlier drive cycles were attempted while the infusion set tubing 72 is clogged or kinked, the fluid pressure upstream of the occlusion (e.g., in the medicine cartridge 120 and in the cap device 130) can be increased. In these circumstances, the flexible membrane 264 that is adjacent to the fluid channel 260 may be substantially deformed (e.g., the membrane 264 will flex downwardly into the air cavity 265 to abut the light transmissive member 254.) In the example depicted by FIG. 19, the interface where the light transmissive member 254 meets the flexible membrane 264 provides different optical results than the previously described interface (FIG. 18) where the light transmissive member 254 meets the air cavity. In particular, the amount of light from the light emitter 253 that is internally reflected at the interface where the light transmissive member 254 meets the flexible membrane 264 is measurably less (as illustrated by the dotted lines in FIG. 19).

Still referring to FIG. 19, the light that is not internally reflected at this interface may pass into the medium of flexible membrane 264 and perhaps into the fluid channel 260. For example, the refractive index of the material of the flexible membrane 264 can be substantially similar to that of the material of the light transmissive member 254. As a result, the light being transmitted through the light transmissive member 254 can pass into the flexible membrane 264 when the membrane 264 flexes into the air cavity 265 and contacts the flat surface of the light transmissive member 254. The light from the light emitter 253 does not undergo total internal reflection at the portion where the flexible membrane 264 interfaces with light transmissive member 254, thereby resulting in reduced amount of light received by the light sensor 258. If any portion of the light is internally reflected, this reduced portion of reflected light continues through the light transmissive member 254 toward a second curved surface 257 and then toward the light sensor 258. Because the amount of light that is internally reflected in the light transmissive member 254 is measurably less, the light sensor 258 can produce detection signals that are different from those described in connection with FIG. 18.

Referring again to FIGS. 18-19, the detection signals from the light sensor 258 can be transmitted via the sensor circuit 252 to the control circuitry 240. The control circuitry 240 receives the signals from the light sensor 258 and uses this data, at least in part, to determine if an occlusion alert should be provided to the user. In the example depicted in FIG. 19, these detection signals may indicate that the fluid pressure in the cap device 130 has risen above the threshold level due to a downstream occlusion.

As previously described, the control circuitry 240 receives the signals from the light sensor 258 and uses this data to determine if an occlusion alert should be provided to the user. For example, the control circuitry 240 may include a detection software module and an alert trigger module stored in one or more memory devices (e.g., on the main processor board 242).

The detection software module may include instructions to use the data signals from the light sensor 258 as input data for a comparative algorithm that determines if an occlusion exists and whether or not to alert the user if an occlusion exists. The comparative algorithm can, for example, compare the data values from the light sensor 258 to an initial value recorded when the pump device 100 was initially activated with no occlusions in the flow path. Alternatively, the comparative algorithm can, for example, average the data values from the light sensor 258 recorded over a predetermined period of time (e.g., 2 minutes, 5 minutes, 10 minutes, 30 minutes, or the like) or over a predetermined number of pump drive cycles (e.g., the last 3 drive cycles, the last 5 drive cycles, the last 10 drive cycles). Then, this average value can be compare to an initial value recorded when the pump device 100 was initially activated with no occlusions in the flow path. These comparative algorithms can be used to reduce the instances of "false alarms" that are provided to the user, and in some cases, can be used to reduce error created by noise in the sensor system. Additionally, or in the alternative, the comparative algorithms can utilize a sensitivity value such as the alarm sensitivity K value described below in connection with FIG. 20. It should be understood from the description herein that, in other embodiments, the detection software module may employ other algorithms to process the data and thereby determine if an occlusion exists.

If the detection software module indicates than an occlusion exists, the control circuitry 240 can activate the alarm trigger module to alert the user. The alarm trigger module can be used to activate the user interface 220 (FIG. 1) to communicate one or more alarms. For example, the alarm trigger module of the control circuitry may be used to activate an audible alarm, a visual alarm (e.g., on the display device 222 as shown in FIG. 1), or a combination thereof. In some embodiments, the alarm trigger module is configured to provide a set of escalating alarms. For example, the first stage of the alarm may include a low intensity audible alert followed by a textual alarm on the display device. If the user does not respond after a predetermined period of time (e.g., 10 seconds, 30 seconds, or the like) and/or a predetermined number of pump system 300 activation cycles (e.g., 3, 5, 6, or the like), the alarm trigger module may then provide a high intensity audible alert (e.g., louder alert) in combination with a visual alarm having image effects on the display device (e.g., a blinking screen, alternating images, or the like). The alarm trigger module may include further stages of alarm if the user does not respond after a predetermined period of time. When the user is alerted to the occlusion in the flow path, the user can inspect the infusion set tubing 72 and the cannula 76 to determine if there is a repairable kink. If the occlusion is substantial, the user can suspend the operation of the infusion pump system 10 and replace the infusion set 70 with a new infusion set 70.

Figure 20:
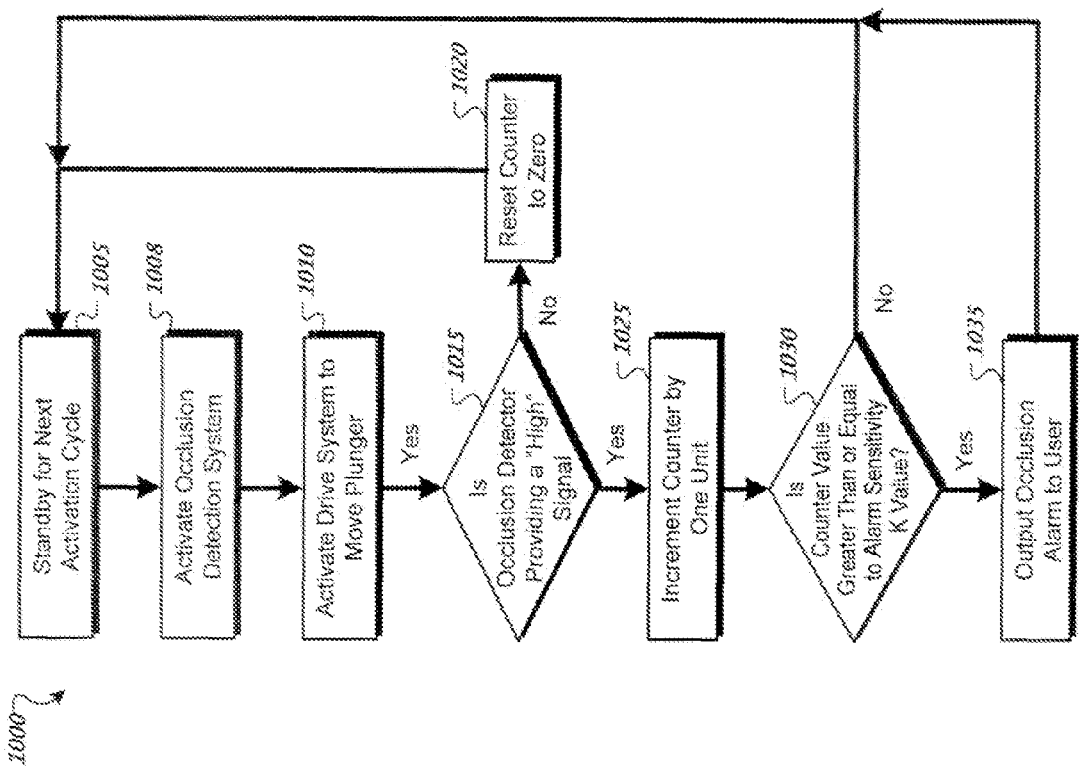
FIG. 20 is a flow diagram depicting an exemplary process used to determine when a user should be alerted to an occlusion, in accordance with some embodiments.

Referring now to FIG. 20, some embodiments of a process 1000 for providing an occlusion alarm to a user can include a number of operations performed by the controller device 200 of the pump assembly 60. In operation 1005, the controller device 200 is in a standby mode in which the pump assembly is awaiting the next activation cycle of the drive system 300. In operation 1008, the occlusion detection system is activated and an optical detection signal indicative of the fluid pressure status is received. For example, as previously described in connection with FIGS. 17-19, the pump system 10 can activate an optical occlusion detection system, such as the optical sensor system 250, to sample the fluid pressure state (e.g., to determine if the pressure within the fluid path is higher than a predetermined threshold). In one example, the optical sensor system 250 can output a "low" signal if the magnitude of the pressure within the fluid path is less than or equal to a predetermined threshold (e.g., the fluid pressure does not cause sufficient flexing of membrane 264 as shown in FIG. 18), and can output a "high" signal if the pressure magnitude is greater than the predetermined threshold (e.g., the fluid pressure causes the flexible membrane 264 to flex as described in FIG. 19). In operation 1010, the drive system 300 is activated. For example, the controller device 200 may activate the drive system 300 to deliver an incremental dosage of medicine in accordance with the basal delivery program, the bolus delivery program, or the like. As previously described, the activation of the drive system 300 causes the plunger 125 to advance within the cartridge 120 (FIG. 2). Advancing the plunger 125 can cause the pressure inside the medicine cartridge 120 to at least temporarily increase, thus expelling fluid out the output port 139, through the flexible tube 72, out the cannula 76 and into the user through the skin. As the fluid is expelled, the pressure within the medicine cartridge returns to an equilibrium pressure, at which point fluid no longer is delivered from the medicine cartridge 120. In the event of an occlusion (e.g., a kink in the flexible tube 72, a blockage in the cannula 76, or the like) the advancing plunger 125 can cause an increase in the fluid pressure, but the expected amount of fluid is not necessarily expelled from the cartridge 120. In these circumstances, the pressure developed within the medicine cartridge 120 during the advancement of the plunger 125 may not be fully relieved.

In operation 1015, the sensor signal received during operation 1008 is evaluated by the controller device 200. (It should be understood that the operation 1015 can be performed before, after, or contemporaneously with operation 1010 so long as it performed after operation 1008.) If the signal provided by the occlusion detection system is a low signal, operation 1020 can be performed so that the controller device 200 resets a counter value to zero. The counter value may be, for example, a numerical value stored in the memory of the controller device 200. Thereafter, the process 1000 returns to operation 1005 to stand by for subsequent activations of the drive system 300. If the sensor signal provided by the occlusion detection system is a "high" signal, operation 1025 is performed so that the controller device 200 incrementally increases the counter value by one unit.

Still referring to FIG. 20, after operation 1025 is performed (so that the counter value was incremented by one unit), the process 1000 can continue to operation 1030 in which the controller device 200 can compare the counter value to a predetermined alarm sensitivity K value. If the counter is less than the sensitivity K value, the process 1000 returns to operation 1005 in which the controller device returns to a standby mode. If the counter is greater than or equal to the sensitivity K value, operation 1035 is performed and the controller device 200 outputs an occlusion alarm to the user.

In some embodiments, the sensitivity K value may be selected so that the occlusion alarm is provided to the user in a timely manner while reducing the likelihood of false alarms (e.g., from transient kinks in the tubing 72 or the like). For example, the sensitivity K value may be selected to be "5" so that the occlusion alarm is output in the event of five or more consecutive high pressure detections. For example, if a user's blood glucose level is high, the risk posed by an occlusion may be significant. As such, the sensitivity of the occlusion detection system may be increased during periods when the monitoring device 50 indicates that the user's blood glucose level is within a designated "high" range (FIG. 1). However, if a user's blood glucose level falls within a "normal" range, the problems associated with false alarms (e.g., false alarms may be a nuisance for the user) may be greater than the need for rapid or immediate occlusion alarms. In these circumstances, the sensitivity of the occlusion detection system may be returned to a standard setting (e.g., moderate sensitivity) when the monitoring device 50 indicates that the user's blood glucose level is within a "normal" range. Such adjustments can be used to decrease the likelihood of false alarms when blood glucose levels are in an acceptable range, while ensuring that the user is promptly alerted to possible occlusions when the blood glucose levels are high and insulin dispensation is an urgent concern.

Figure 21:
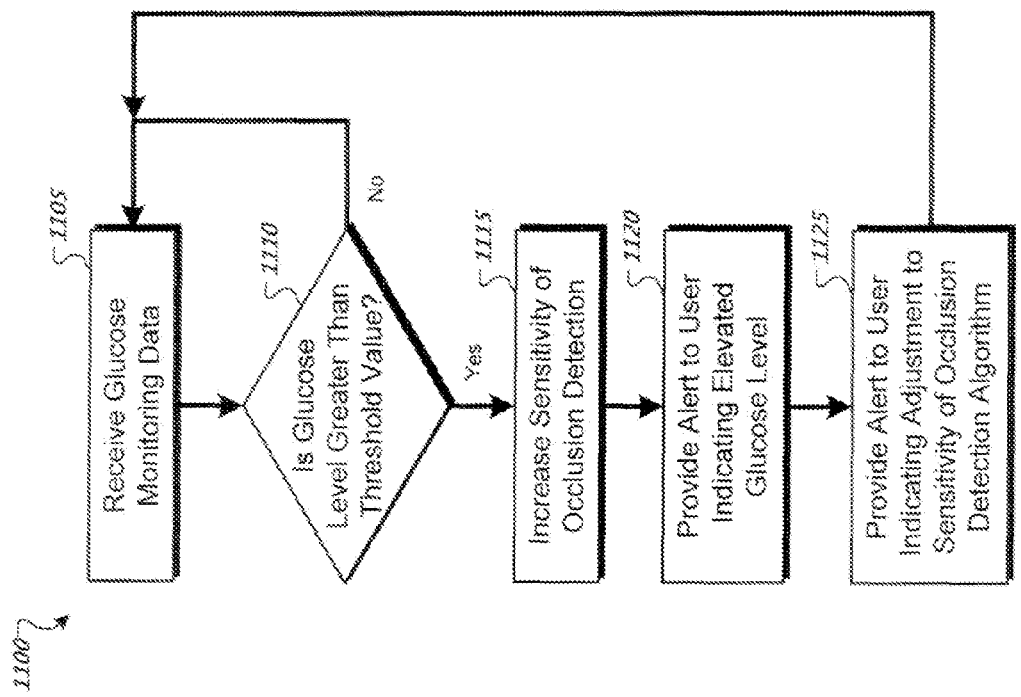
FIG. 21 is a flow diagram depicting an exemplary process used to determine whether adjustments are to be made to the sensitivity of an occlusion detection system based (at least in part) on glucose data, in accordance with some embodiments.

Referring to FIG. 21, some embodiments of a process 1100 can be utilized to adjust the sensitivity of an occlusion detection system (e.g., the optical detection system 250) based (at least in part) on information indicative of a user's blood glucose level. The process 1100 may include a number of operations that are performed by the controller device 200 of the pump system 10. In operation 1105, the controller device 200 may receive glucose data from, for example, the glucose monitoring device 50. As previously described, the monitoring device 50 may communicate wirelessly with the controller device 200. In operation 1110, the controller device 200 can compare the glucose level obtained during operation 1105 to a predetermined threshold value (e.g., a glucose level representing an upper limit of a normal glucose range). If the glucose level is not greater than the threshold value, the process 1100 can return to operation 1105 and stands by for subsequent glucose monitoring data. If the glucose level is greater than the threshold value, operation 1115 is performed and the sensitivity of the occlusion detection system is increased. In some embodiments, the controller device 200 increases the sensitivity of the occlusion detection system in operation 115 by decreasing the alarm sensitivity K value (described in connection with FIG. 12). In one example, the alarm sensitivity K value is decreased from "5" to "3", meaning that only three consecutive high pressure detections are required to activate the occlusion alarm (instead of five).

In some embodiments, the pump system 10 may indicate to the user that the detected glucose level is at an elevated state. In operation 1120, the controller device can provide an alert to the user indicating that the user's glucose level is elevated (refer, for example, to FIG. 1). Also, in some embodiments, the pump system 10 may indicate to the user that the occlusion detection system was adjusted. For example, in operation 1125, the controller device 200 can provide an alert to the user indicating that the sensitivity of the occlusion detection system has been increased (refer, for example, to FIG. 1). After completion of operation 1125, process 1100 can return to operation 1105, entering the stand by mode. It should be understood that, after the user's blood glucose level returns to the normal range, the sensitivity of the occlusion detection system may likewise return to a previous value condition (in this example, the sensitivity K value can be returned to "5", meaning that five or more consecutive high pressure detections are required to activate the occlusion alarm).

In addition (or in the alternative) to the process 1100 described in connection with FIG. 21, some embodiments of the controller device 200 (employing the optical detection system 250) can operate to adjust the sensitivity of the occlusion detection system using one or more processes as described in connection with FIGS. 14, 15, and 16. For example, the sensitivity of the optical detection system 250 can be increased based on information indicative of a high rate of increase in the blood glucose levels. As described in connection with FIG. 14, the controller device 200 can determine, based on current and previously detected glucose levels, a rate at which a user's blood glucose level is rising. The rate of increase in the user's blood glucose rate can then be compared to a predetermined threshold rate. As previously described in connection with FIG. 14, if the determined rate is greater than the threshold rate, the sensitivity of the optical occlusion detection system 250 can be increased by decreasing the alarm sensitivity K value.

In another example, the sensitivity of the optical detection system 250 can be decreased based on information indicative of low blood glucose levels. As described in connection with FIG. 15, the controller device 200 can receive measurements indicative of a user's blood glucose level from the glucose monitoring device 50 and compare these measurements to a predetermined threshold value. If a detected glucose level is less than the threshold level, the sensitivity of the optical occlusion detection system 250 can be decreased by increasing the alarm sensitivity K value.

In yet another example, the sensitivity of the optical detection system 250 can be decreased based on information indicative of a significant rate of decrease of blood glucose levels. As described in connection with FIG. 16, the controller device 200 can determine, based on current and past measured glucose data, a rate at which a user's blood glucose level is falling. The rate of decrease in the user's blood glucose rate can then be compared to a predetermined threshold rate. If the determined rate is greater than the threshold rate, the sensitivity of the optical occlusion detection system 250 can be decreased by increasing the alarm sensitivity K value.

Thus, the pump system 10 can be used to communicate information indicative of a user's blood glucose level (or another characteristic) to the controller device 200. In such circumstances, the controller device 200 can be configured to adjust the sensitivity of the occlusion detection system based (at least in part) on the information indicative of the user's blood glucose level. Such adjustments can be used to decrease the likelihood of false alarms when blood glucose levels are in an acceptable range, while ensuring that the user is promptly alerted to possible occlusions when the blood glucose levels are high and insulin dispensation is an urgent concern.

A number of embodiments of the invention have been described. Nevertheless, it will be understood that various modifications may be made without departing from the spirit and scope of the invention. Accordingly, other embodiments are within the scope of the following claims.

What is claimed is:

1. A method of operating an insulin infusion pump system, comprising:
    activating an occlusion detection system to detect a fluid pressure in a flow path extending from an insulin reservoir in a portable insulin pump apparatus to a user, the portable insulin pump apparatus including a pump drive system to dispense insulin through the flow path to the user;
    activating the pump drive system to deliver an incremental dosage of insulin;
    in response to a signal from the occlusion detection system indicating a fluid pressure greater than a threshold pressure limit for the incremental dosage of insulin, increasing a counter value stored in a memory device of the portable insulin pump apparatus while foregoing output of an occlusion alarm;
    in response to a signal from the occlusion detection system indicating a fluid pressure less than or equal to the threshold pressure limit for each incremental dosage of insulin, resetting the counter value to zero;
    adjusting a threshold counter value based on glucose information; and
    in response to the counter exceeding the threshold counter value, outputting the occlusion alarm from portable insulin pump apparatus to the user.

2. The method of claim 1, wherein the portable insulin pump apparatus comprises: a portable pump housing that receives insulin for dispensation to the user, and a controller that provides electrical signals to activate the pump drive system to dispense the insulin from the portable pump housing.

3. The method of claim 2, wherein the controller operates the occlusion detection system that detects the fluid condition in the flow path.

4. The method of claim 2, wherein the controller is removably attachable to the portable pump housing, the controller comprising: a controller housing that removably attaches to the portable pump housing, a user interface that includes a display device, and an electrical connector that mates with a complementary electrical connector of the portable pump housing when the controller housing is removably attached to the portable pump housing.

5. The method of claim 1, wherein the flow path comprises the insulin reservoir in which the insulin is retained, at least a portion of a cap device that secures to a portable pump housing of the portable insulin pump apparatus so as to cover an external opening of the portable pump housing, and an infusion set tube that extends from the cap device to the user.

6. The method of claim 1, wherein the occlusion detection system comprises at least one of a pressure transducer and a pressure switch to communicate signals to a controller of the portable insulin pump apparatus indicative of fluid pressure in the flow path of the insulin.

7. The method of claim 1, wherein the occlusion detection system comprises an optical sensor arranged proximate to the flow path of the insulin.

8. A method of operating an insulin infusion pump system, comprising:
- activating an occlusion detection system to detect a fluid condition in a flow path extending from an insulin reservoir in a portable insulin pump apparatus to a user, the portable insulin pump apparatus including a pump drive system to dispense insulin through the flow path to the user;
- activating the pump drive system to deliver a first incremental dosage of insulin;
- in response to a first signal from the occlusion detection system indicating an occlusion in the flow path, increasing a counter value stored in a memory device of the portable insulin pump apparatus while foregoing output of an occlusion alarm;
- activating the pump drive system to deliver one or more subsequent incremental dosages of insulin;
- in response to a predetermined quantity of consecutive signals from the occlusion detection system indicating the occlusion in the flow path, outputting the occlusion alarm from portable insulin pump apparatus to the user
- receiving glucose information from a monitoring device, the glucose information being indicative of a detected blood glucose level of the user; and
- adjusting a sensitivity of the occlusion detection system based upon the glucose information from the monitoring device, wherein the sensitivity of the occlusion detection system is adjusted by altering a value of the predetermined quantity of consecutive signals from the occlusion detection system indicating the occlusion.

9. The method of claim 8, wherein the sensitivity of the occlusion detection system is increased in response to glucose information received from the monitoring device that indicates the detected blood glucose level is greater than a predetermined value.

10. The method of claim 9, further comprising outputting an alarm via a user interface to indicate the detected blood glucose level is outside of a normal range.

11. The method of claim 9, further comprising outputting an alarm via a user interface to indicate a change to the occlusion detection system.

12. The method of claim 8, wherein the sensitivity of the occlusion detection system is increased in response to glucose information received from the monitoring device that indicates the detected blood glucose level is rising at a rate greater than a predetermined rate.

13. The method of claim 12, further comprising outputting an alarm via a user interface to indicate a change to the occlusion detection system.

14. The method of claim 8, wherein the sensitivity of the occlusion detection system is decreased in response to glucose information received from the monitoring device that indicates the detected blood glucose level is less than a predetermined value.

15. The method of claim 14, further comprising outputting an alarm via a user interface to indicate the detected blood glucose level is outside of a normal range.

16. The method of claim 14, further comprising outputting an alarm via a user interface to indicate a change to the occlusion detection system.

17. The method of claim 8, wherein the sensitivity of the occlusion detection system is decreased in response to glucose information received from the monitoring device that indicates the detected blood glucose level is decreasing at a rate greater than a predetermined rate.

18. The method of claim 17, further comprising outputting an alarm via a user interface to indicate a change to the occlusion detection system.

19. The method of claim 8, further comprising resetting the counter value to zero in response to a signal from the occlusion detection system indicating no occlusion in the flow path.

20. The method of claim 8, wherein each signal from the occlusion detection system indicating the occlusion is representative of a detected pressure in the flow path that is greater than a threshold pressure limit.

* * * * *